(12) United States Patent
Churchill et al.

(10) Patent No.: US 8,034,930 B2
(45) Date of Patent: Oct. 11, 2011

(54) BORON-DIPYRRIN COMPOUNDS COMPRISING THIENYL GROUPS, PREPARATION METHOD THEREOF AND CHEMOSENSOR COMPRISING THE SAME

(75) Inventors: David G. Churchill, Daejeon (KR); Kibong Kim, Daejeon (KR); Shin Hei Choi, Daejeon (KR)

(73) Assignee: Korea Advanced Institute of Science and Technology, Daejeon (KR)

( * ) Notice: Subject to any disclaimer, the term of this patent is extended or adjusted under 35 U.S.C. 154(b) by 356 days.

(21) Appl. No.: 12/289,834

(22) Filed: Nov. 5, 2008

(65) Prior Publication Data

US 2009/0203923 A1 Aug. 13, 2009

(30) Foreign Application Priority Data

Feb. 12, 2008 (KR) .................. 10-2008-0012766

(51) Int. Cl.
*C07F 5/02* (2006.01)
(52) U.S. Cl. ..................................... 544/229
(58) Field of Classification Search .................. 544/229
See application file for complete search history.

(56) References Cited

U.S. PATENT DOCUMENTS 5,248,782 A 9/1993 Haugland et al.

OTHER PUBLICATIONS

Choi et al., Inorganic Chemistry, 2007, 46(25):10564-10577.*
Brückner, C., et al., "Synthesis of meso-phenyl-4,6-dipyrrins, preparation of their Cu(II), Ni(II), and Zn(II) chelates, and structural characterization of bis[mieso-phenyl-4,6-dipyrrinato]Ni(II)", Can, J. Chem., vol. 74, pp. 2182-2193, (1996).
Qi, X. et al., *New BODIPY Derivatives as OFF_ON Fluorescent Chemosensor and Fluorescent Chemodosimeter for $Cu^{2+}$: Cooperative Selectivity Enhancement toward $Cu^{2+}$*. Journal of Organic Chemistry 2006, 71, 2881-2884.
Rurack, K. et al., *A Selective and Sensitive Fluoroionophore for $Hg^{II}$, $Ag^{I}$, and $Cu^{II}$ with Virtually Decoupled Fluorophore and Receptor Units*. Journal of the American Chemical Society 2000, 122, 968-969.
Coskun, A. et al., *Bis(2-pyridyl)-Substituted Boratriazaindacene as an NIR-Emitting Chemosensor for Hg(II)*. Organic Letters 2007, 9, 607-609.
Yuan, M. et al., *A Colorimetric and Fluorometric Dual-Modal Assay for Mercury Ion by a Molecule*. Organic Letters 2007, 9, 2313-2316.
Moon, S.Y. et al., *New $Hg^{2+}$-Selective Chromo- and Fuoroionophore Based upon 8-Hydroxyquinoline*. Journal of Organic Chemistry 2004, 69, 181-183.
Lee, C. et al., *One-Flask Synthesis of Meso-Substituted Dipyrromethanes and Their Application in the Synthesis of Trans-Substituted Porphyrin Building Blocks*. Tetrahedron 1994, 50, 11427-11440.
Littler, B.J. et al., *Refined Synthesis of 5-Substituted Dipyrromethanes*. Journal of Organic Chemistry 1999, 64, 1391-1396.
Kee, H.L. et al., *Structural Control of the Photodynamics of Boron-Dipyrrin Complexes*. Journal of Physical Chemistry B 2005, 109, 20433-20443.
Choi, S.H. et al., *X-ray diffraction, DFT, and spectroscopic study of N,N'-difluoroboryl-5- (2-thienyl) dipyrrin and fluorescence studies of related dipyrromethanes, dipyrrins and $BF_2$-dipyrrins and DFT conformational study of 5- (2-thienyl)dipyrrin*. The Journal of Chemical Crystallography 2007, 37, 315-331.
Choi, S.H. et al., *$Cu^{2+}$ Colorimetric Sensing and Fluorescence Enhancement and $Hg^{2+}$ Fluorescence Diminution in "Scorpionate"-like Tetrathienyl-Substituted Boron-Dipyrrins*. Inorganic Chemistry 2007, 46, 10564-10577.

* cited by examiner

*Primary Examiner* — Rei-tsang Shiao
(74) *Attorney, Agent, or Firm* — The Nath Law Group; Tanya E. Harkins; Mihsuhn Koh

(57) ABSTRACT

Disclosed are (i) a boron-dipyrrin compound having thienyl groups, (ii) a preparation method thereof and (iii) a chemosensor comprising the boron-dipyrrin compound having thienyl groups. More particularly, the present invention provides a boron-dipyrrin compound having thienyl group, furyl ($OC_4H_3$) group or selyl ($SeC_4H_3$) group, which is represented by the following formula (1), a preparation method thereof and a chemosensor comprising the above boron-dipyrrin compound having thienyl groups, characterized in that the chemosensor exhibits variations in colors and fluorescent properties caused by reaction of the boron-dipyrrin compound with metal ions, including, but not limited to, $Cu^{2+}$ and $Hg^{2+}$:

3-(R)-4,4-di(R)-8-(R)-4-bora-3a,4a-diaza-s-indacene formula (1)

wherein R is any one selected from 2-thienyl group and 3-thienyl group.

2 Claims, 11 Drawing Sheets

Fig. 1
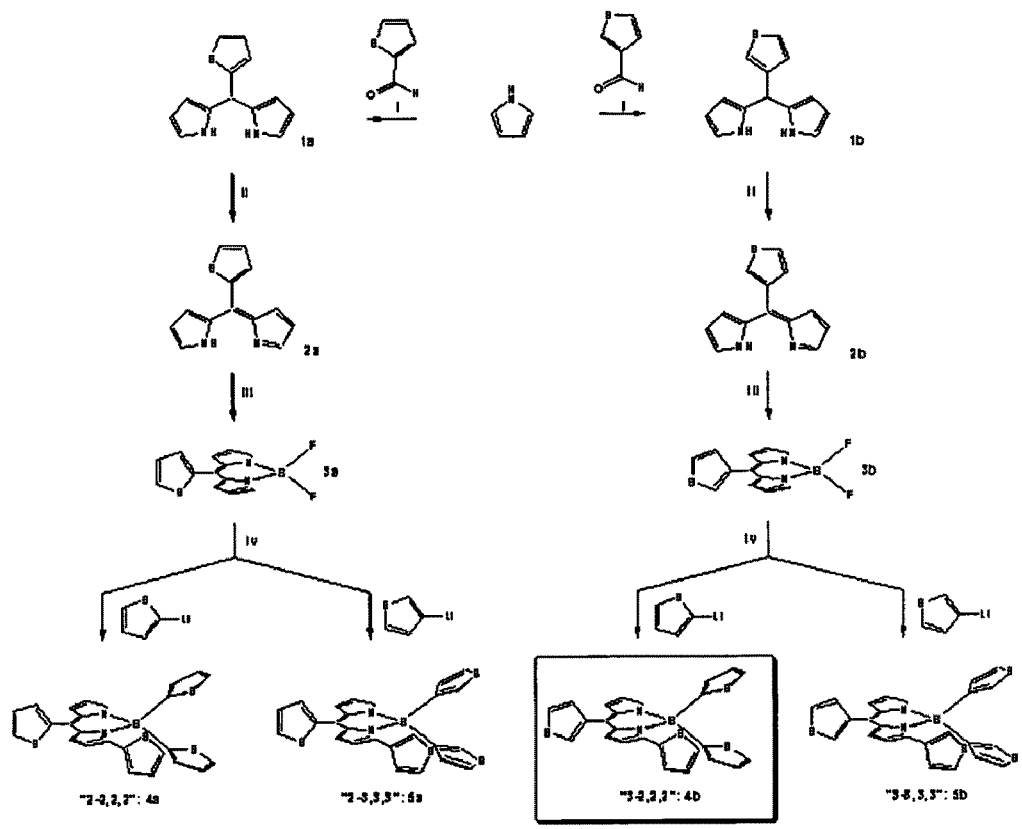
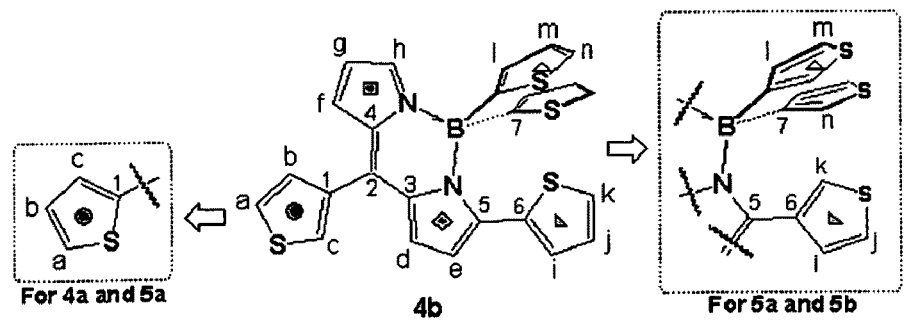

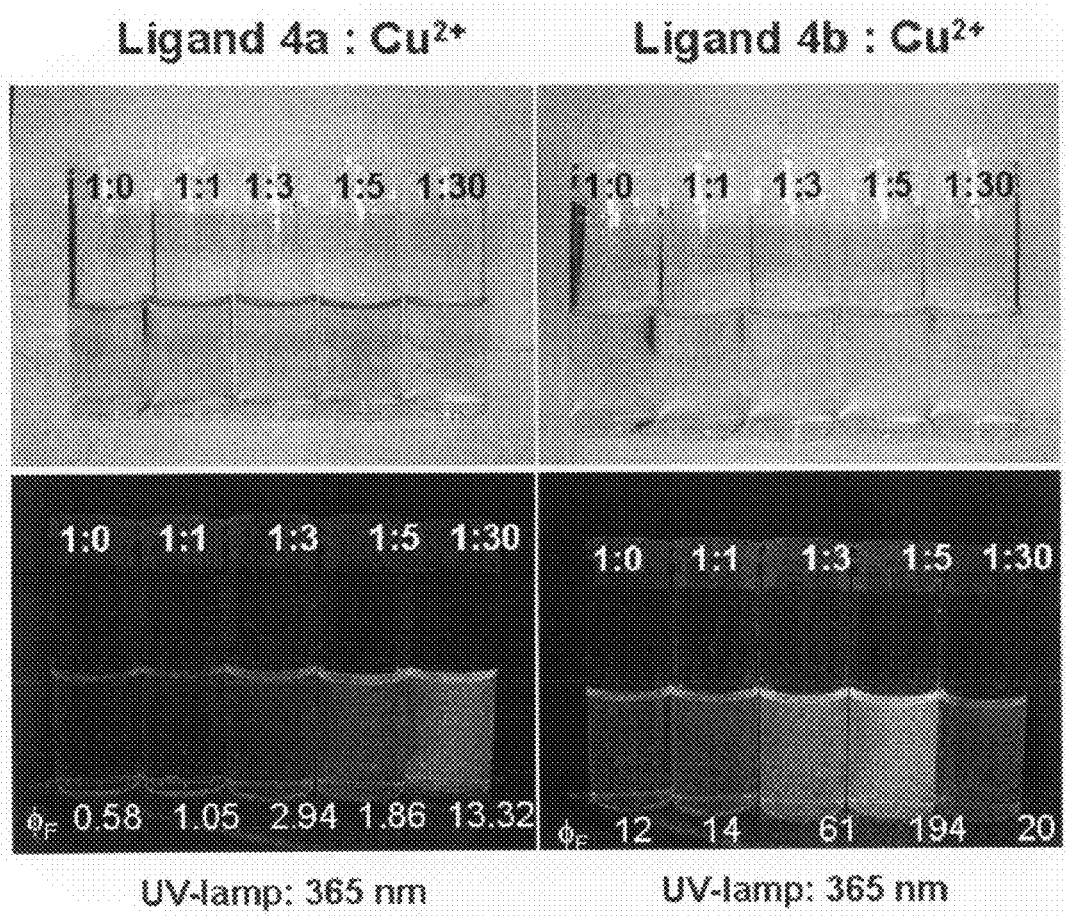

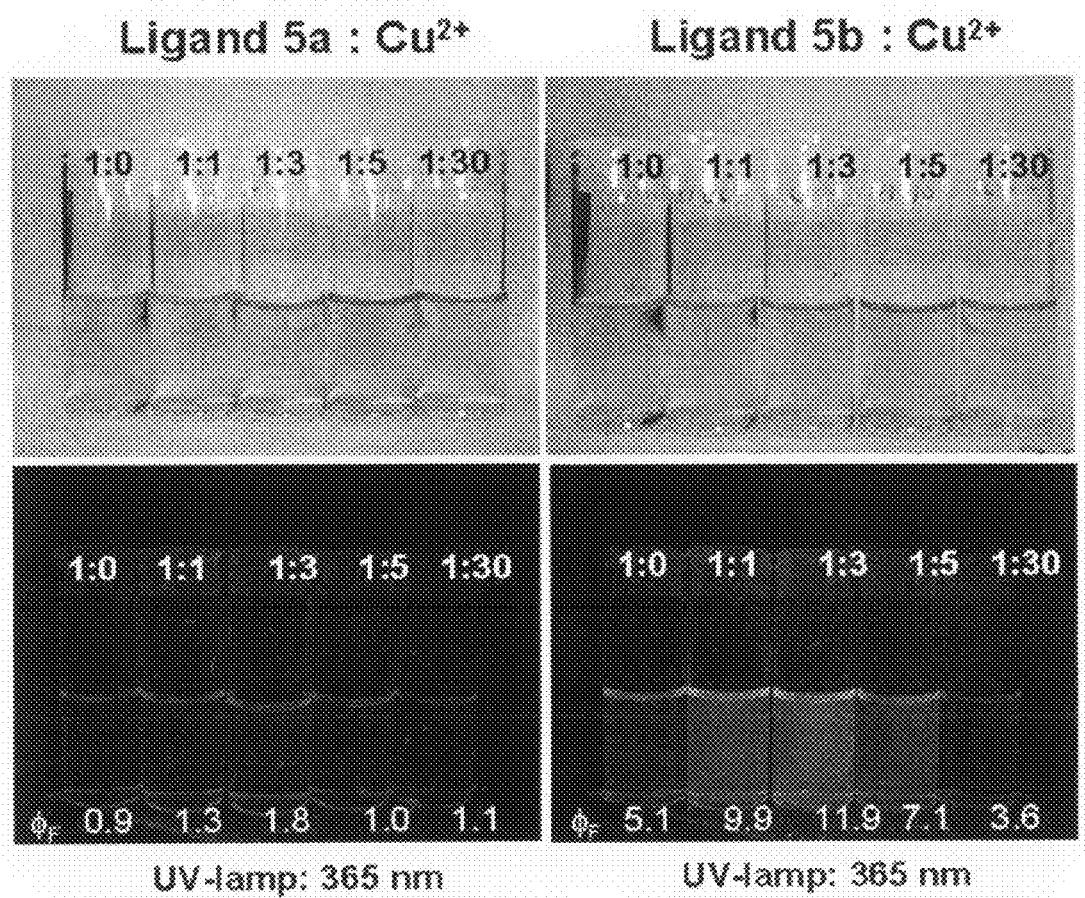

BORON-DIPYRRIN COMPOUNDS COMPRISING THIENYL GROUPS, PREPARATION METHOD THEREOF AND CHEMOSENSOR COMPRISING THE SAME

BACKGROUND OF THE INVENTION

This application claims priority to Korean Patent Application No. 2008-12766, filed on Feb. 12, 2008, in the Korean Intellectual Property Office, the entire contents of which are hereby incorporated by reference.

1. Field of the Invention

The present invention relates to boron-dipyrrin compounds that include thienyl groups, preparation methods thereof and chemosensors comprising the boron-dipyrrin compounds having thienyl groups, more particularly, to a boron-dipyrrin compound having thienyl groups, represented by the following formula (1), a preparation method thereof and a chemosensor comprising the above boron-dipyrrin compound having thienyl groups, characterized in that the chemosensor exhibits variations in colors and fluorescent properties caused by interaction of the boron-dipyrrin compound with metal ions:

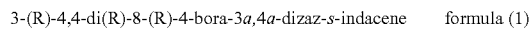

3-(R)-4,4-di(R)-8-(R)-4-bora-3*a*,4*a*-dizaz-*s*-indacene    formula (1)

wherein R is any one selected from 2-thienyl group, 3-thienyl group, furyl (OC4H3) group and selyl (SeC4H3) group.

2. Description of the Related Art

Boron-dipyrrin compounds having thienyl groups have structural similarities to a material usually known as BODIPY (also known as: boron dipyrrin, BF2-dipyrrin, or 4,4-difluoro-bora-3a,4a-diaza-s-indacene). Such species that contain thienyl type groups that give UV-vis spectra that are red shifted, or bathochromically shifted have been represented previously by a patent ("Long wavelength heteroaryl-substituted dipyrrometheneboron difluoride dyes" Haugland, R. P.; Kang, H. C. (Molecular Probes, Inc., USA). U.S. Pat. No. 5,248,782, 1993.)

BODIPY is also previously known to belong to broad class of organic dyeing materials. In general, the dyeing materials have structures modified from a basic compound selected from a group consisting of: anthracene; pyrene; cyclodextrin; calixarene; fluorescein; quinoline; rhodamine; azulene; pyridine; thiazole; thiadiazole; thiophene; cyclam; BODIPY (boron dipyrrin); ferrocene; carbohydrate; peptide, etc. Such materials with superior fluorescence are generally used in biological studies such as, for example, researches for surface-marking bio-masses with the dyeing materials and monitoring biological reactions that give rie to fluorescent reporters.

Dyeing materials with fluorescence mostly have degree of fluorescence (that is, fluorescent level) increased, decreased or eliminated by chemical interactions or reactions, therefore, are often called "chemosensors." Many chemosensors have been developed and/or reported in the related arts, for example, there were recent reports to demonstrate sensors, switches, dosimeters and so on for the cupric ion, $Cu^{2+}$, and mercuric ion, $Hg^{2+}$.

Among metal ions, the cupric ion, $Cu^{2+}$, is broadly distributed in natural resources and have a variety of roles in the ecosystem. Mercury is also naturally discovered in mineral form. However, mercury and mercuric ions $Hg^{2+}$ which were used in industrial applications and have accumulated in soils and/or water in the form of methyl mercury $CH_3HgCl$ with neurotoxicity, are now considered as significant pollutants which threaten the ecological health of the environment.

Therefore, it is very important and strongly required to develop novel ionic detection systems to detect both of $Cu^{2+}$ and $Hg^{2+}$.

Boron-dipyrrin type substances with $Cu^{2+}$ and $Hg^{2+}$ detection abilities have been disclosed in technical documents including, for example: Qi, X. et al., Journal of Organic Chemistry 2006, 71, 2881-2884; Rurack, K. et al., Journal of the American Chemical Society 2000, 122, 968-969; Coskun, A. et al., Organic Letters 2007, 9, 607-609; Yuan, M. et al., Organic Letters 2007, 9, 2313-2316; Moon, S. Y. et al., Journal of Organic Chemistry 2004, 69, 181-183, etc. But, these substances have typical coordinate units in the form of pyridine or crown to detect metal ions.

A simple method for production of the eighth (8) 4,4-difluoro-bora-3a,4a-diaza-s-indacene carbon site substituted $BF_2$-dipyrrin was reported by Lindsey et al., (see Lee, C. H. et al, Tetrahedron 1994, 50, 11427-11440 and Littler, B. J. et al., Journal of Organic Chemistry 1999, 64, 1391-1396).

Also, Kee disclosed a method of improving fluorescent level of $BF_2$-dipyrrin while altering the eighth (8) 4,4-difluoro-bora-3a,4a-diaza-s-indacene carbon site with different substituents, in Kee, H. L. et al., Journal of Physical Chemistry B 2005, 109, 20433-20443.

SUMMARY OF THE INVENTION

Accordingly, the present invention is directed to solve the problem of conventional propositions as described above and relates to boron-dipyrrin compounds with specific substituents and preparation methods thereof.

An object of the present invention is to provide a chemosensor substrate for detecting metal ions as observed by change of spectral properties. The substrate is composed of a boron-dipyrrin compound having specific substituents.

More particularly, the present invention provides a boron-dipyrrin compound having thienyl groups, furyl group (OC4H3)or selyl (SeC4H3) group.

The present invention also provides a method for preparation of a boron-dipyrrin compound having thienyl groups.

Another object of the present invention is to provide a chemosensor which comprises the above boron-dipyrrin compound having thienyl groups, furyl (OC4H3) group or selyl (SeC4H3) group or a boron-dipyrrin compound having thienyl groups produced by the above method for preparation of the boron-dipyrrin compound having thienyl groups.

Still a further object of the present invention is to provide a chemosensor capable of easily detecting metal ions, especially, copper ions $Cu^{2+}$ and/or mercuric ions $Hg^{2+}$, which comprises the above boron-dipyrrin compound having thienyl groups or a boron-dipyrrin compound having thienyl groups, furyl (OC4H3) group or selyl (SeC4H3) group produced by the above method for preparation of the boron-dipyrrin compound having thienyl groups.

The boron-dipyrrin compound having thienyl groups of the present invention has structural specificity in that three of four thienyl groups form a space in the form of an attacking scorpion (two pincers and a stinging tail) to sense metal ions, more particularly, molecules substituted by three thienyl groups have a pattern similar to the shape of a scorpion; this site formed by the thienyl groups plays a role of coordinate site to receive a metal ion. Especially, such metal ions can be visibly detected through variation of colors and alteration of fluorescent levels by sensing copper ions $Cu^{2+}$ and/or mercuric ions $Hg^{2+}$ as the fluorphore substrate changes its electronic properties.

The boron-dipyrrin compound having thienyl group of the present invention exhibits metal ion detection ability as well as properties responsible for bonding reversibility, thereby having favorable selectivity and reversibility required for chemical sensors, that is, chemosensors.

Accordingly, the boron-dipyrrin compound having thienyl group of the present invention is potentially applicable to novel chemosensor materials, which can detect metal ions such as copper ions $Cu^{2+}$ and/or mercuric ions $Hg^{2+}$, so that the present inventive compound can be efficiently used in removing environmental pollutants containing, for example, $Cu^{2+}$ and/or $Hg^{2+}$.

BRIEF DESCRIPTION OF THE DRAWINGS

These and other objects, features, aspects, and: advantages of preferred embodiments of the present invention will be more fully described in the following detailed descriptions, taken in conjunction with the accompanying drawings. In the drawings:

FIG. 1 is a processing view of an embodiment for production of a boron-dipyrrin compound having four thienyl groups;

FIG. 4a is a set of photographs showing variation of colors and alteration of fluorescent levels by sensing copper ions $Cu^{2+}$ for compounds (4a) and (4b) prepared in Examples 1 and 2, respectively;

FIG. 4b is a set of photographs showing variation of colors and alteration of fluorescent levels by sensing copper ions $Cu^{2+}$ in compounds (5a) and (5b) prepared in Examples 3 and 4, respectively;

DETAILED DESCRIPTION OF THE INVENTION

Figure 2A:
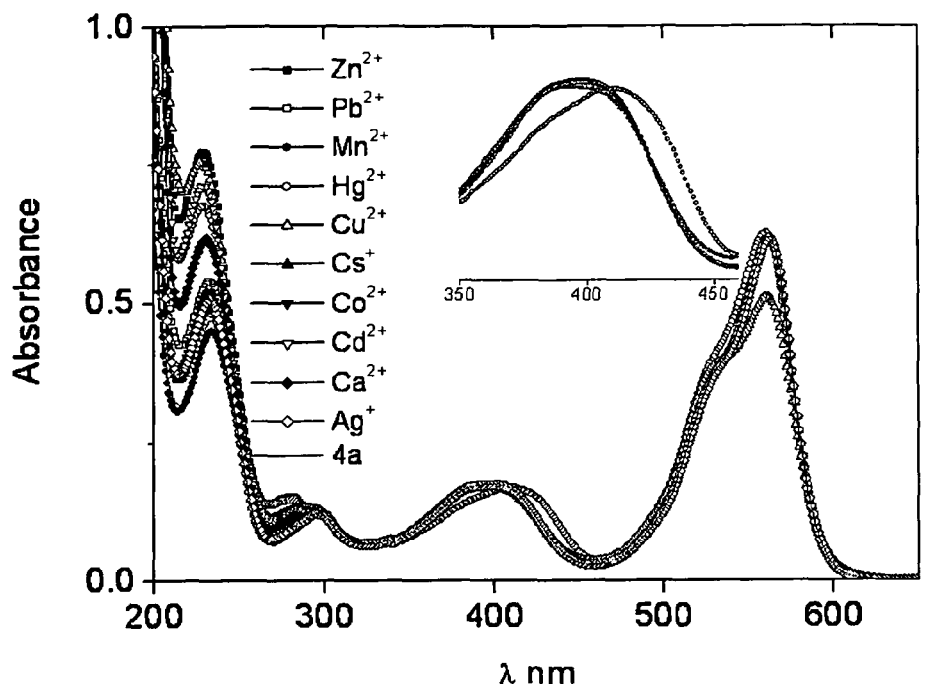
FIG. 2a is an absorption spectrum illustrating selectivities to metal ions for compound (4a) prepared in Example 1.
Figure 2B:
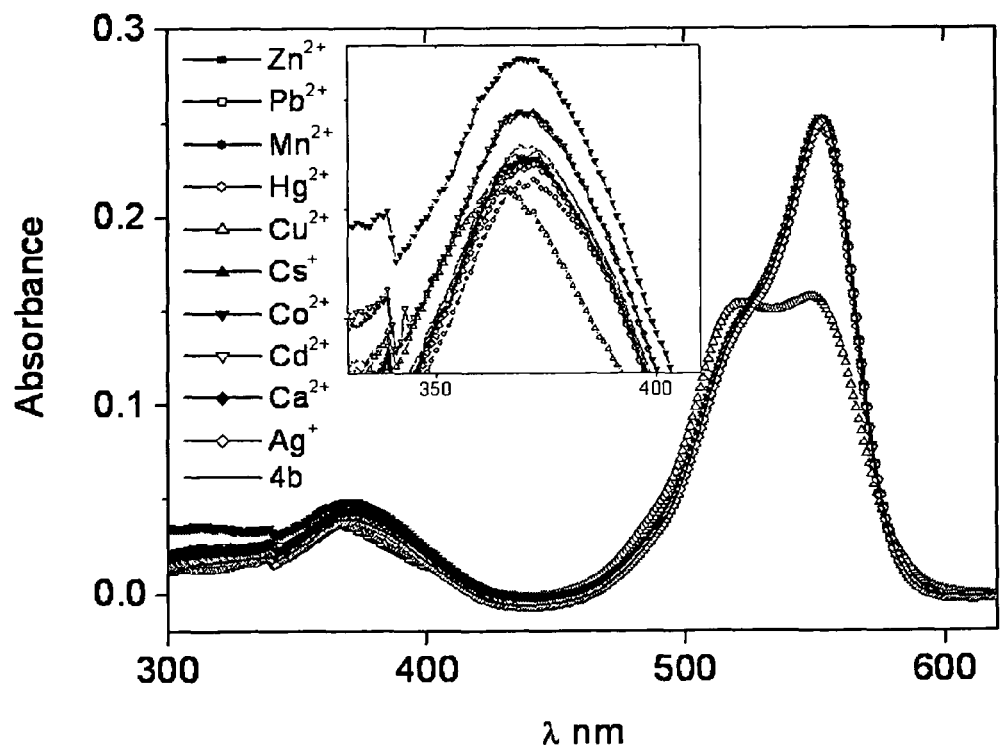
FIG. 2b is an absorption spectra illustrating selectivities to metal ions for compound (4b) prepared in Example 2.
Figure 2C:
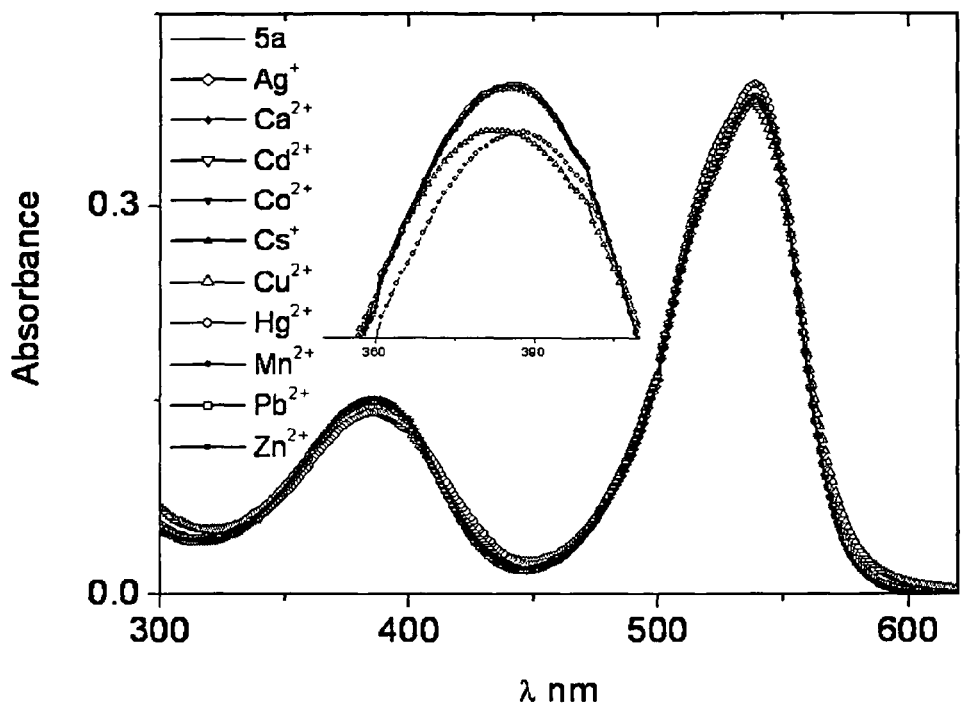
FIG. 2c is an absorption spectrum illustrating selectivities to metal ions in a compound (5a) prepared in Example 3.
Figure 2D:
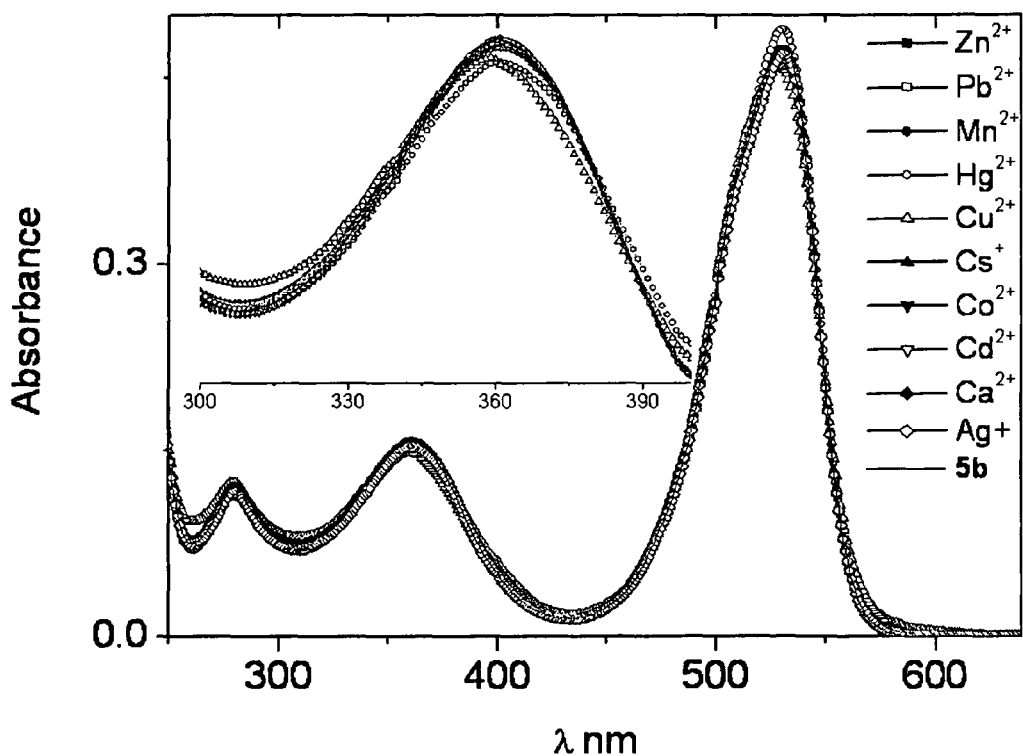
FIG. 2d is an absorption spectrum illustrating selectivities to metal ions in a compound (5b) prepared in Example 1.
Figure 3A:
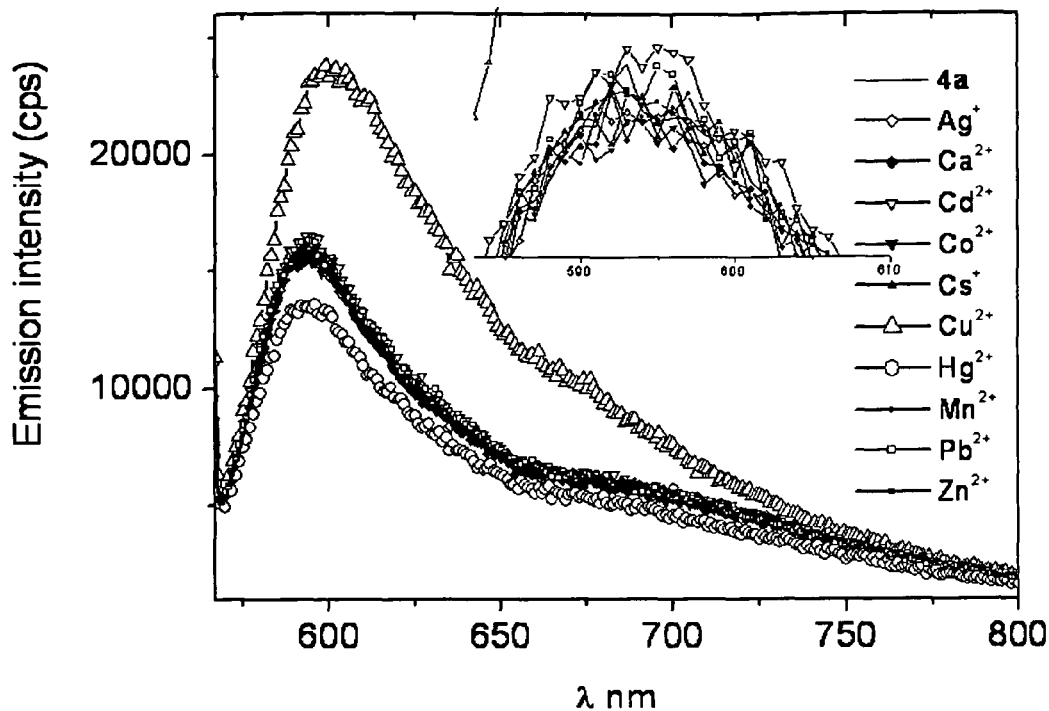
FIG. 3a is a fluorescence spectrum illustrating selectivities to metal ions in a compound (4a) prepared in Example 1.
Figure 3B:
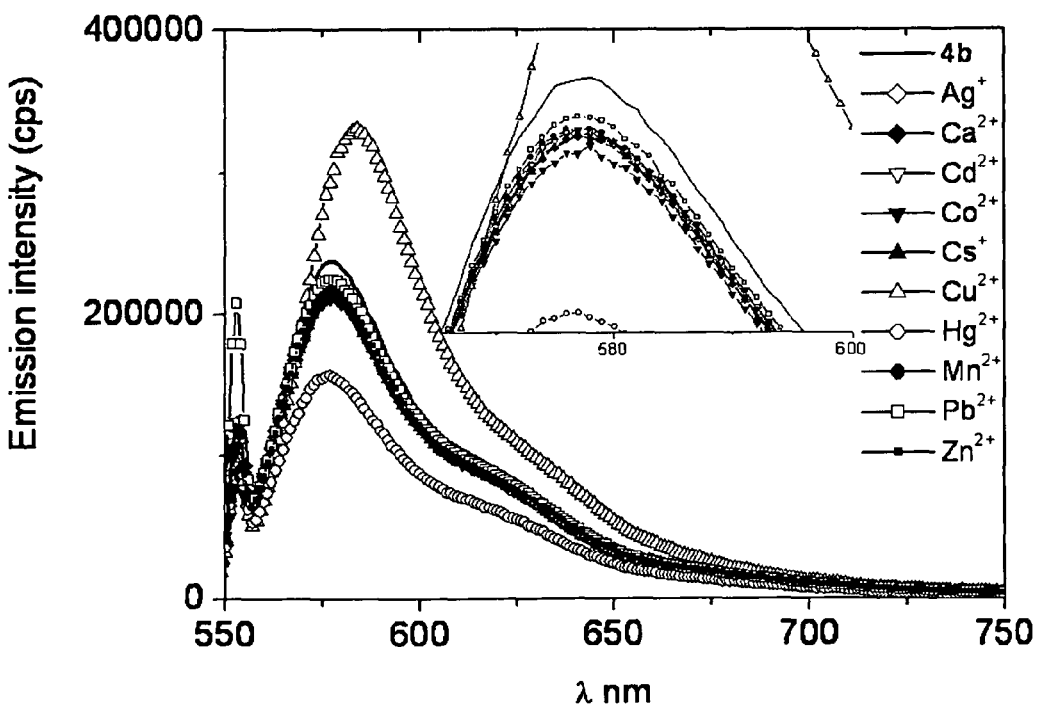
FIG. 3b is a fluorescence spectrum illustrating selectivities to metal ions in a compound (4b) prepared in Example 2.
Figure 3C:
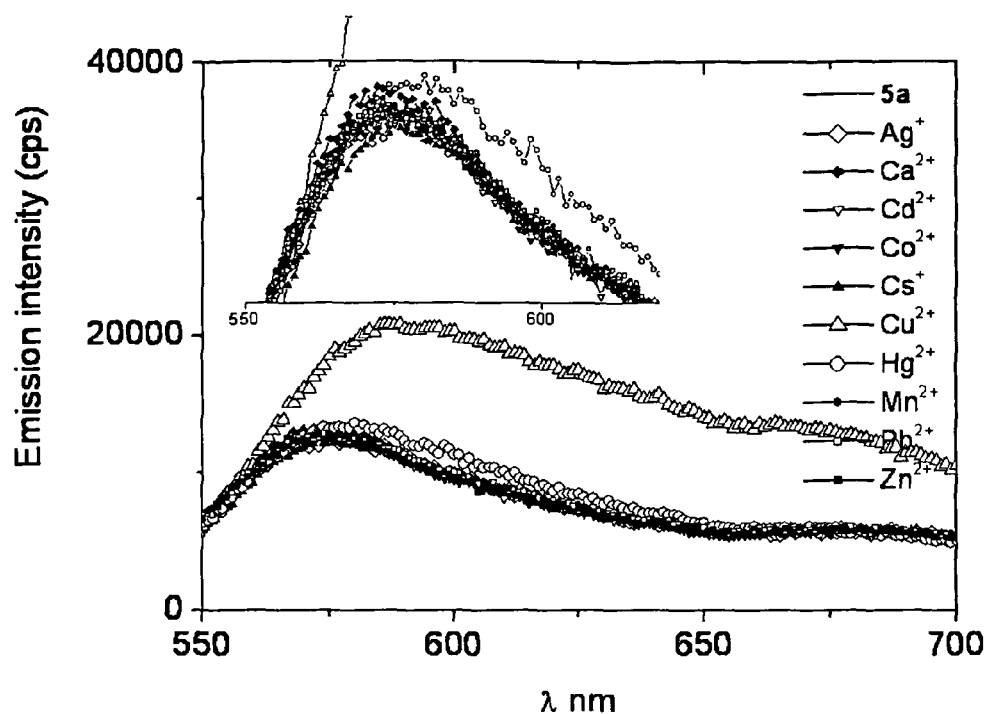
FIG. 3c is a fluorescence spectrum illustrating selectivities to metal ions in a compound (5a) prepared in Example 3.
Figure 3D:
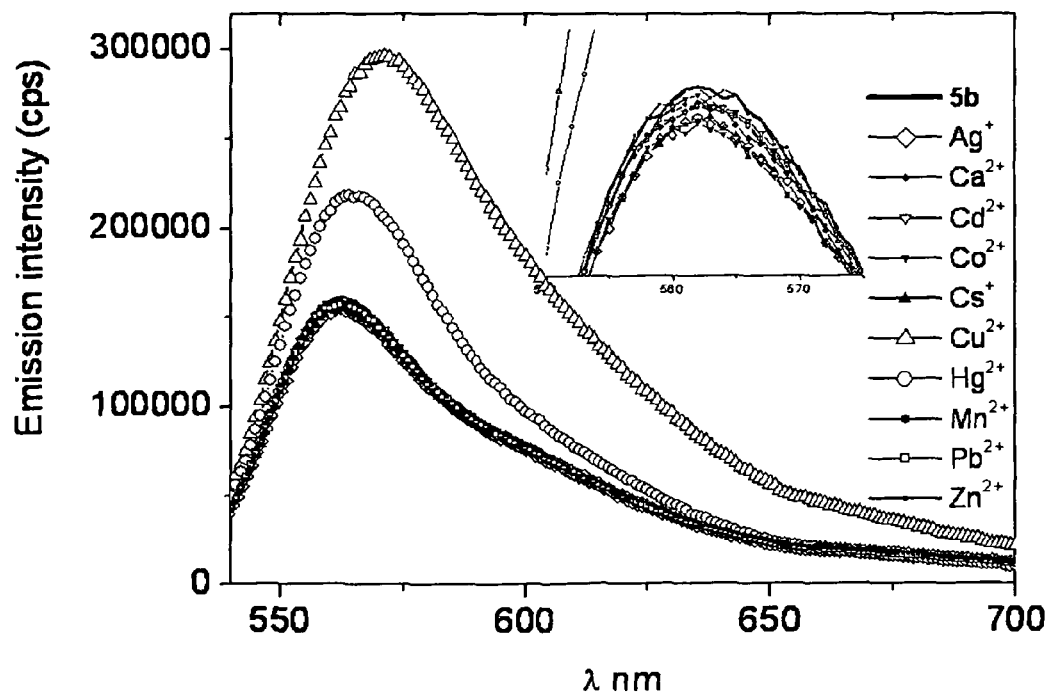
FIG. 3d is a fluorescence spectrum illustrating selectivities to metal ions in a compound (5b) prepared in Example 4.
Figure 5A:
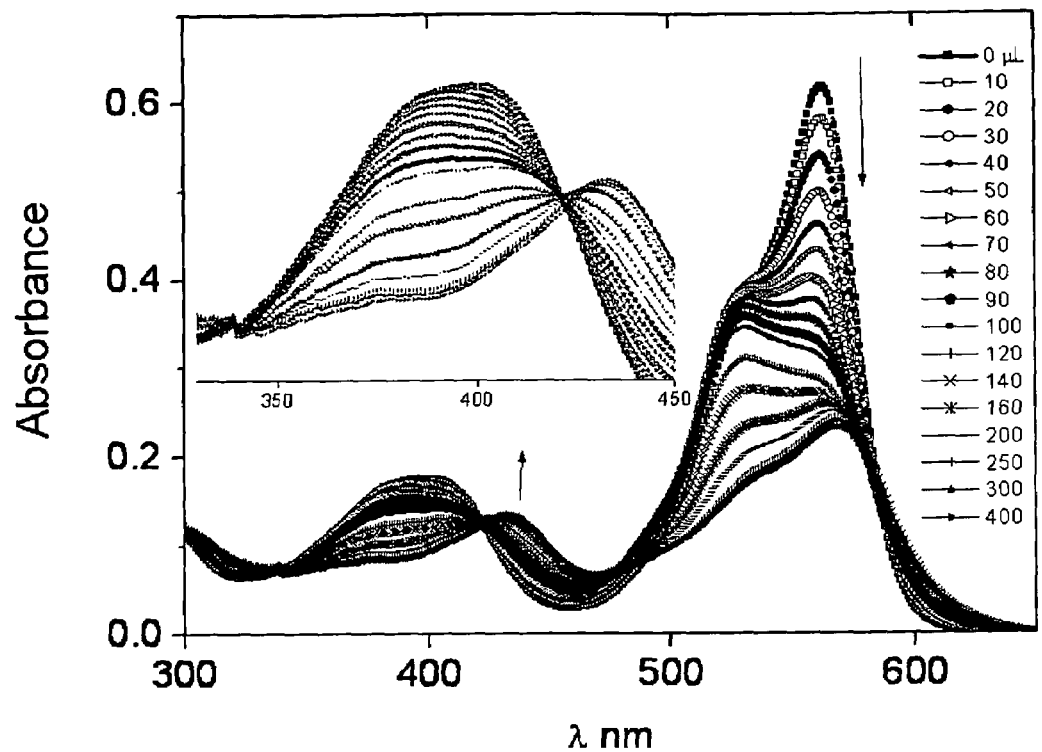
FIG. 5a is a set of spectra illustrating the variation of the absorption bands by titration of copper ions $Cu^{2+}$ in compound (4a) prepared in Example 1.
Figure 5B:
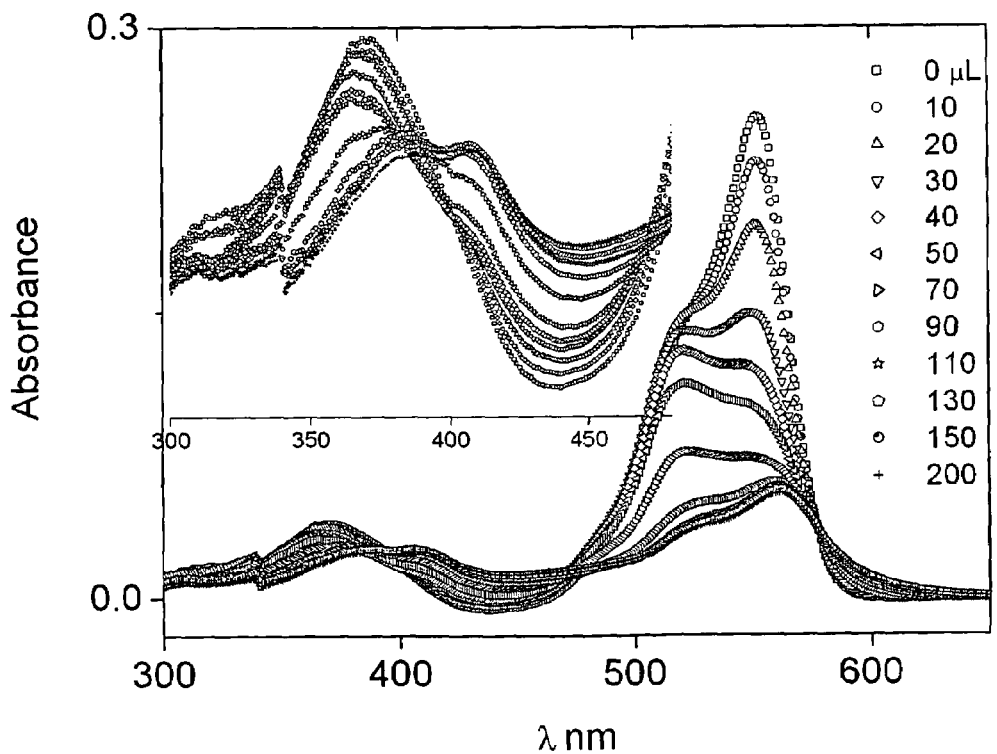
FIG. 5b is a set of spectra illustrating the variation of the absorption bands by titration of copper ions $Cu^{2+}$ in compound (4b) prepared in Example 2.
Figure 5C:
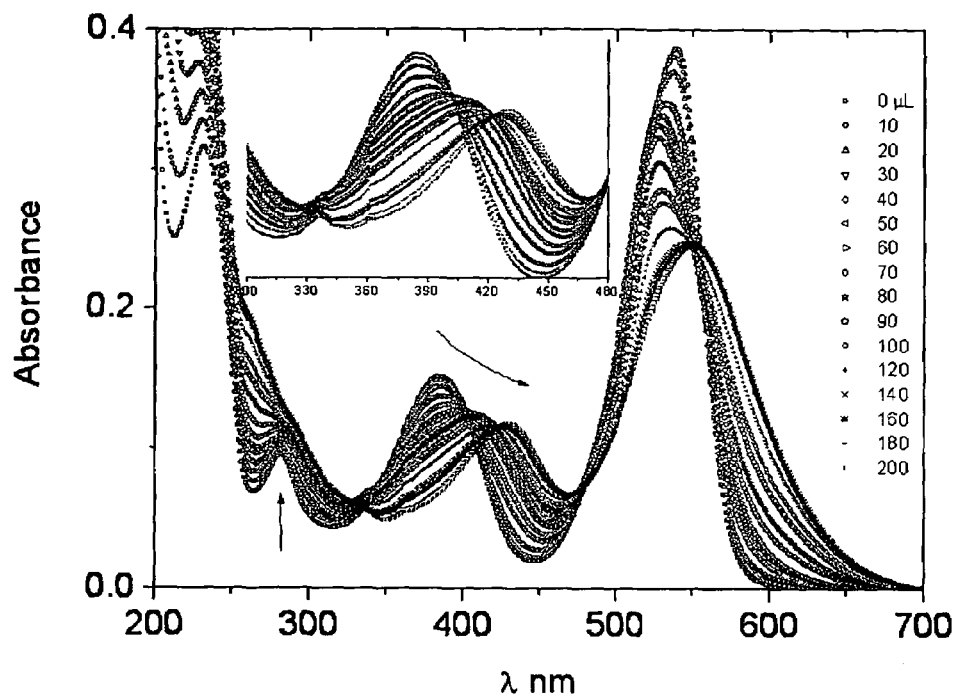
FIG. 5c is a set of spectra illustrating variation of absorption spectra by titration of copper ions $Cu^{2+}$ in compound (5a) prepared in Example 3.
Figure 5D:
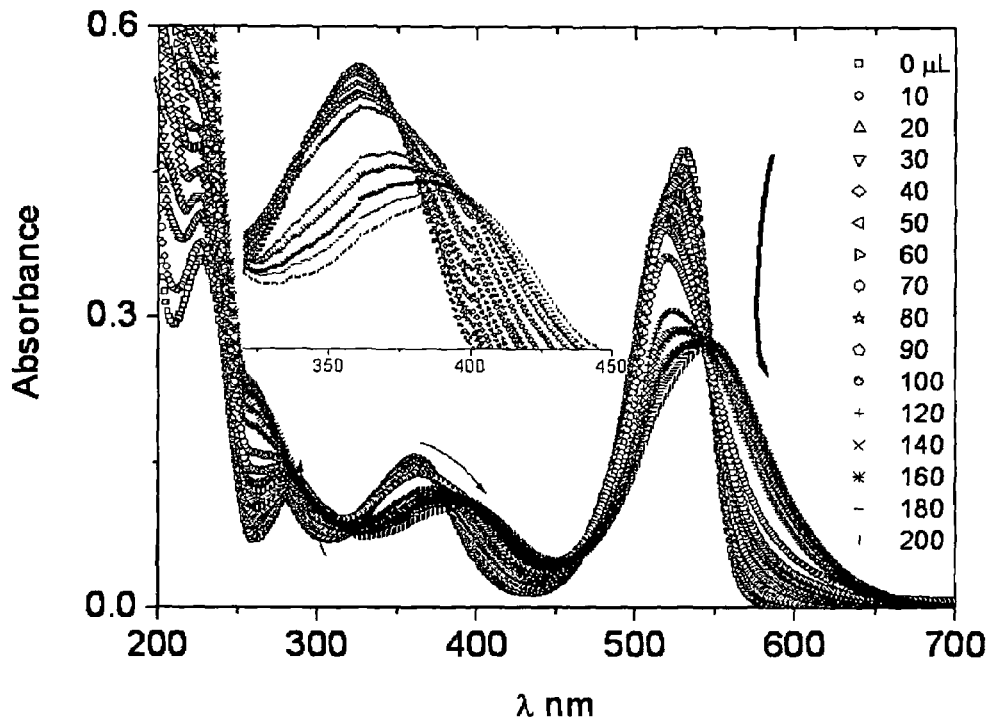
FIG. 5d is a set of spectra illustrating variation of absorption spectra by titration of copper ions $Cu^{2+}$ in compound (5b) prepared in Example 4.

The present invention describes a boron-dipyrrin compound having thienyl groups.

More particularly, the present invention provides a boron-dipyrrin compound containing four thienyl groups with structural specificity, characterized in that three of the thienyl groups, furyl ($OC_4H_3$) group or selyl ($SeC_4H_3$) group form a space in the form of a scorpion.

The boron-dipyrrin compounds having thienyl groups of the present invention has structural specificity in that three of four thienyl groups form a space in the form of a scorpion to sense metal ions, wherein a molecule with three substituted thienyl groups has a form similar to the shape of a scorpion (two pincers and a stinging tail) and the space formed by these thienyl groups plays a role of coordinate site to receive the metal ions.

According to the present invention, the boron-dipyrrin compound having thienyl group is represented by the following formula (1):

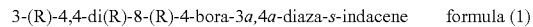

3-(R)-4,4-di(R)-8-(R)-4-bora-3a,4a-diaza-s-indacene　　formula (1)

wherein R is any one selected from 2-thienyl group, 3 thienyl group, furyl ($OC_4H_3$) group and selyl ($SeC_4H_3$) group.

The present invention also provides a boron-dipyrrin compound containing four thienyl groups with structural specificity in that three of the thienyl groups form a space in the form of a scorpion, represented by the formula (1):

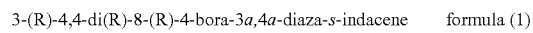

3-(R)-4,4-di(R)-8-(R)-4-bora-3a,4a-diaza-s-indacene　　formula (1)

wherein R is any one selected from 2-thienyl group and 3-thienyl group.

The above boron-dipyrrin compound having thienyl group represented by the formula (1) can be prepared by substituting difluoro group and eighth (8) 4,4-difluoro-bora-3a,4a-diaza-s-indacene carbon site of a compound represented by the following formula (2), with any one selected from 2-thienyl group, 3-thienyl group, furyl ($OC_4H_3$) group and selyl ($SeC_4H_3$) group:

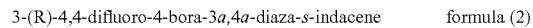

3-(R)-4,4-difluoro-4-bora-3a,4a-diaza-s-indacene　　formula (2)

wherein R is any one selected from 2-thienyl group, 3-thienyl group, furyl ($OC_4H_3$) group and selyl ($SeC_4H_3$) group.

The present invention provides a method for preparation of a boron-dipyrrin compound having thienyl group.

More particularly, the present invention provides a method for the preparation of a boron-dipyrrin compound containing four thienyl groups with structural specificity in that three of the thienyl groups form a space in the form of a scorpion (two pincers and a stinging tail).

The present invention also provides a method for preparation of a boron-dipyrrin compound having thienyl group, which is represented by the formula (1):

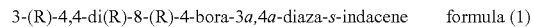

3-(R)-4,4-di(R)-8-(R)-4-bora-3a,4a-diaza-s-indacene　　formula (1)

wherein R is any one selected from 2-thienyl group and 3-thienyl group.

According to the present invention, the method for preparation of the boron-dipyrrin compound containing four thienyl groups with structural specificity in that three of the thienyl groups form a space in the form of a scorpion, is represented by the formula (1):

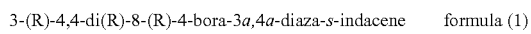

3-(R)-4,4-di(R)-8-(R)-4-bora-3a,4a-diaza-s-indacene  formula (1)

wherein R is any one selected from 2-thienyl group, 3-thienyl group, furyl ($OC_4H_3$) group and selyl ($SeC_4H_3$) group.

The above preparation method comprises reaction of a compound represented by the following formula (2) with a material having thienyl group to produce the boron-dipyrrin compound having thienyl group which is represented by the formula (1);

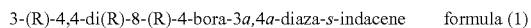

3-(R)-4,4-di(R)-8-(R)-4-bora-3a,4a-diaza-s-indacene  formula (1)

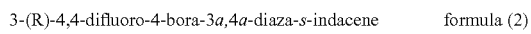

3-(R)-4,4-difluoro-4-bora-3a,4a-diaza-s-indacene  formula (2)

wherein R is any one selected from 2-thienyl group, 3-thienyl group, furyl ($OC_4H_3$) group and selyl ($SeC_4H_3$) group.

The above material having thienyl group may include materials having any one functional group selected from 2-thienyl group, 3-thienyl group, furyl ($OC_4H_3$) group and selyl ($SeC_4H_3$) group.

Examples of the materials having thienyl group may comprise any one selected from 2-thienyl lithium and 3-thienyl lithium.

The reaction between compound represented by the formula (2) and the material having thienyl comprises, for example: reacting 1 to 10 molar equivalents of the material having thienyl group with 1 mole of compound represented by the formula (2) to produce the boron-dipyrrin compound represented by the formula (1) according to the present invention, that is, the boron-dipyrrin compound containing four thienyl groups with structural specificity in that three of the thienyl groups form a space in the form of a scorpion and, more particularly, in that a molecule formed by three thienyl groups has specific structure similar to the shape of a scorpion (two pincers and a stinging tail) and the space formed by these thienyl groups plays a role of coordinate site to receive metal ions.

The reaction between compound represented by the formula (2) and the material having thienyl group can be performed by adding 1 to 10 moles of the material having thienyl group to 1 mole of compound represented by the formula (2) and agitating the mixture at $-90°$ C. to $-0°$ C. under an inert gas atmosphere.

Preferably, the reaction between compound represented by the formula (2) and the material having thienyl group is performed by adding 1 to 10 moles of the material having thienyl group to 1 mole of compound represented by the formula (2) and agitating the mixture at $-90°$ C. to $-0°$ C. under an inert gas atmosphere until the material having thienyl group is completely reacted.

The inert gas comprises any one selected from a group consisting of nitrogen (N), helium (He), neon (Ne) and argon (Ar).

FIG. 1 is a schematic processing view illustrating a method for preparation of a boron-dipyrrin compound according to the present invention, which contains four thienyl groups, has structural specificity in that three of the thienyl groups form a space in the form of a scorpion, and is represented by the formula (1).

Referring to FIG. 1, boron-dipyrrin compounds having thienyl groups (4a), (4b), (5a) and (5b) can be produced from starting materials of compounds (3a) and (3b) as described in the following examples.

Another embodiment of the present invention comprises a chemosensor comprising the boron-dipyrrin compound having thienyl group of the present invention, which is represented by the formula (1).

Especially, the present invention provides a chemosensor comprising the boron-dipyrrin compound represented by the formula (1), which contains four thienyl groups and has structural specificity in that three of the thienyl groups form a space in the form of a scorpion.

Still a further embodiment of the present invention comprises a chemosensor comprising a boron-dipyrrin compound having thienyl group, which was produced by the above preparation method according to the present invention and is represented by the formula (1).

Especially, the present invention provides a chemosensor comprising a boron-dipyrrin compound represented by the formula (1), which was produced by the above preparation method according to the present invention and which contains four thienyl groups and has structural specificity in that three of the thienyl groups form a space in the form of a scorpion.

The boron-dipyrrin compound having thienyl group contained in the chemosensor of the present invention has selectivities to metal ions.

The present inventive chemosensor exhibits variations in colors and fluorescent levels by reaction of the boron-dipyrrin compound having thienyl group represented by the formula (1) with metal ions. For example, when a material represented by the formula (1) is dissolved in an organic solvent to prepare a solution (1), metal ions are added to the same organic solvent as the above solvent to prepare another solution (2) and the solution (1) is mixed with the solution (2), the solution (1) shows variation from pink to colorless together with an increase or decrease of fluorescent brightness. In this case, the used organic solvent can be any one selected from a group consisting of tetrahydrofuran (THF), methylene chloride, ethyl alcohol, n-hexane, acetone and acetate. The boron-dipyrrin compound having a thienyl group represented by the formula (1) according to the present invention has high solubility in the above organic solvent while having lower solubility in water. But, some water solubility can be shown by dissolution of compounds into a solvent mixture of water (50% by volume) and and acetonitrile (50% by volume). The boron-dipyrrin compound having thienyl group represented by the formula (1) in the organic solvent has a pink color.

The boron-dipyrrin compound having thienyl group contained in the chemosensor of the present invention has selectivities to copper ions $Cu^{2+}$ and/or mercuric ions $Hg^{2+}$ as the metal ions.

The present inventive chemosensor exhibits variation of colors and alteration of fluorescent levels by reaction of the boron-dipyrrin compound having thienyl group represented by the formula (1) with metal ions such copper ions $Cu^{2+}$ and/or mercuric ions $Hg^{2+}$. For example, the chemosensor in specific indicator solutions shows variation of colors from pink to colorless condition and increase or decrease of fluorescent brightness.

The boron-dipyrrin compound having thienyl group, the preparation method thereof and the chemosensor comprising the boron-dipyrrin compound having thienyl group are preferably provided under desired conditions as described above so as to accomplish the objects of the present invention.

Hereafter, the present invention will become apparent from the following examples and experimental examples with reference to the accompanying drawings. However, these are intended to illustrate the invention as preferred embodiments of the present invention and do not limit the scope of the present invention.

EXAMPLE 1

Preparation of 3-(2-thienyl)-4,4-di(2-thienyl)-8-(2-thienyl)-4-bora-3a,4a-diaza-s-indacene [4a]

A compound (4a) was prepared by reacting a compound (3a) with 2-thienyl lithium according to the following reaction scheme 1:

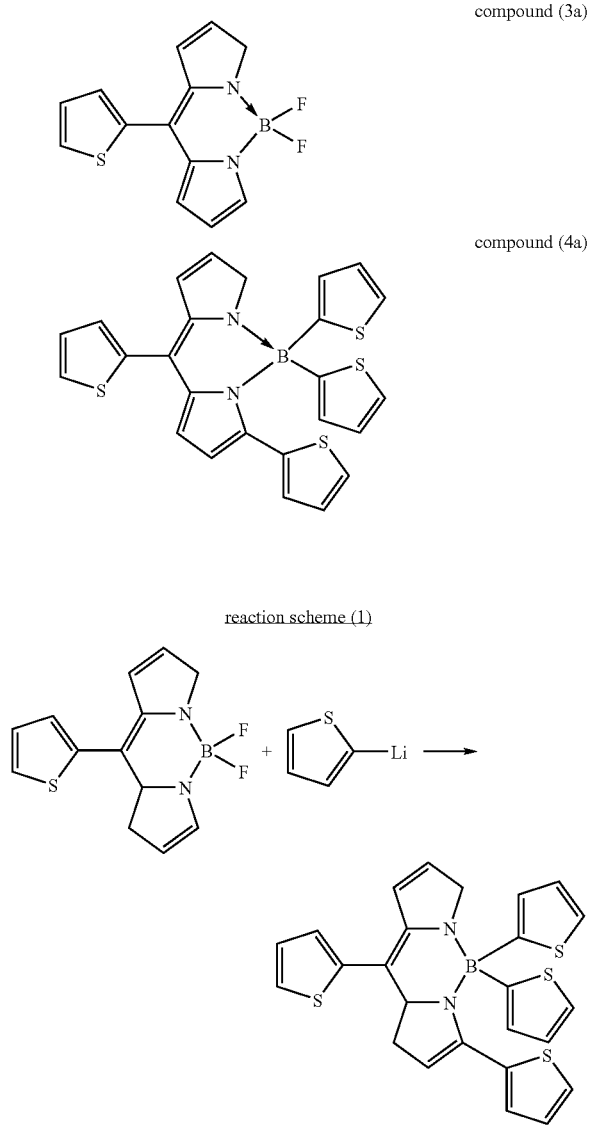

reaction scheme (1)

More particularly, compound (3a) which was prepared by a typical method involving reports by Lindsey (Lee, C. H.; Lindsey, J. S. Tetrahedron 1994, 50, 11427-11440. Littler, B. J.; et al. J. Org. Chem. 1999, 64, 1391-1396.) and Dolphin (Bruckner, C. et al., Can. J. Chem. 1996, 74, 2182-2193.) and known in the Journal of Chemical Crystallography 2007, 37, 315, (1.35 g, 4.75 mmol) was dissolved in 50 mL of anhydrous tetrahydrofuran (THF) and this mixture was agitated at −78° C. for 10 minutes under Ar atmosphere. After drop-wise adding 30 mL of a 1.0 M diluted 2-thienyllithium solution at 1 mL/sec to the agitated solution containing THF and again agitating the reaction mixture at −78° C. for 10 minutes under Ar atmosphere, the prepared solution was left without further treatment until temperature of the mixture comprising compound (3a) and 2-thienyl lithium reached room temperature.

After monitoring that compound (3a) was completely reacted through TLC (thin layer chromatography), 20 mL of distilled water was added to the above mixture solution to terminate the reaction.

After extraction of the mixture solution with dichloromethane, the resulting organic layer was dried using magnesium sulfide while vacuum drying and removing the solvent, that is, dichloromethane, and then the residue underwent purification using a silica column. In this procedure, the residue was developed by passing through a column three times while flowing a mixture solution of hexane and dichloromethane in relative ratio by volume of 1:1. A dark pink portion was collected and subjected to PTLC (preparative thin layer column chromatography) and recrystallization to produce a pure compound of 3-(2-thienyl)-4,4-di(2-thienyl)-8-(2-thienyl)-4-bora-3a,4a-diaza-s-indacene (4a) (0.7 g, yield: 31%). Melting point: 163° C. $^1$H NMR (CD$_2$Cl$_2$: δ 5.32) 7.72 (dd, $^3J_{H-H}$=5.0, $J_{H-H}$=0.8 Hz, 1H$_b$), 7.62 (d, $^3J_{H-H}$=4.0 Hz, 1H$_c$), 7.58 (s, 1H$_h$), 7.48 (d, $^3J_{H-H}$=4.6 Hz, 1H$_d$), 7.30 (m, 2H$_n$), 7.28 (s, 1H$_a$), 7.25 (dd, $^3J_{H-H}$=0.6, $^4J_{H-H}$0.6 Hz 1H$_k$), 7.21 (dd, $^3J_{H-H}$=4.5, $^4J_{H-H}$=0.9 Hz, 1H$_f$), 7.04 (d, $^3J_{H-H}$= 3.3 Hz, 2H$_1$), 6.96 (m, 2H$_m$), 6.88 (d, $^3J_{H-H}$=4.6 Hz, 1H$_e$), 6.87 (s, 1H$_i$), 6.74 (dd, $^3J_{H-H}$=4.8, $^3J_{h-h}$=4.0 Hz, 1H$_j$), 6.49 (dd, $^3J_{H-H}$=4.0, $J_{H-H}$=1.9 Hz, 1H$_g$); $^{13}$C NMR (CD$_2$Cl$_2$: δ 53.8) 152.4 (t, $^1J_{C-H}$=8.8 Hz, 1C$_5$), 144.5 (dt, $^1J_{C-H}$=185.0, $^3J_{C-H}$=9.0 Hz, 1C$_h$), 137.5 (s, 1C$_2$), 136.8 (t, $^2J_{C-H}$=9.0 Hz, 1C$_3$), 135.4 (p, $^2J_{C-H}$5.6 Hz, 1C$_1$), 134.5 (m, J$_{C-H}$=5.6 Hz, 1C$_6$), 132.9 (m, 1C$_4$), 132.8 (ddd, $^1J_{C-H}$=169.6 Hz, $^2J_{C-H}$=9.3 Hz, $^3J_{C-H}$=6.1 Hz, 1C$_c$), 132.0 (ddd, $^1J_{C-H}$= 163.4 Hz, $^3J_{C-H}$=9.2 Hz, $^3J_{C-H}$=6.0 Hz, 1C$_i$), 131.0 (dm, $^1J_{C-H}$~160 Hz, 1C$_1$), (dm, $^1J_{C-H}$~160 Hz, 1C$_d$), 130.7 (ddd, $^1J_{C-H}$=200, $^2J_{C-H}$=9.2, $^2J_{C-H}$=6.1 Hz, 1C$_b$), 129.0 (dm, $^1J_{C-H}$= 211.3 Hz, 1C$_k$), 128.5 (m, 1C$_f$), 128.2 (dt, $^1J_{C-H}$= 171.0, $^2J_{C-H}$=10.1 Hz, 1C$_a$), 127.6 (dm, $^1J_{C-H}$=161.0 Hz, 1C$_j$), 127.5 (dm, $^1J_{C-H}$=161.0 Hz, 2C$_m$), 127.1 (dm, $^1J_{C-H}$= 201.2 Hz, 2C$_n$), 122.3 (dd, $^1J_{C-H}$=175.2, $^2J_{C-H}$=3.6 Hz, 1C$_e$), 118.4 (ddd, $^1J_{C-H}$=174.8, $^2J_{C-H}$=8.9, $^2J_{C-H}$=3.5 Hz, 1C$_g$). $^{11}$B NMR (F$_3$B o OEt$_2$: δ 0.00) −3.59 (s), MALDI-TOF m/z (M$^+$): 484.04 (calc.) 483.99 (obs.), Anal. Calc. for C$_{25}$H$_{17}$BN$_2$S$_4$: C 61.98, H 3.54, and N 5.78, found: C 63.44, H 3.81, and N 6.00.

EXAMPLE 2

Preparation of 3-(2-thienyl)-4,4-di(2-thienyl)-8-(3-thienyl)-4-bora-3a,4a-diaza-s-indacene [4b]

A compound (4b) was prepared by reacting a compound (3b) with 2-thienyl lithium according to the following reaction scheme 2:

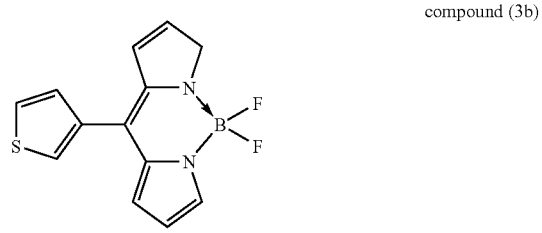

compound (3b)

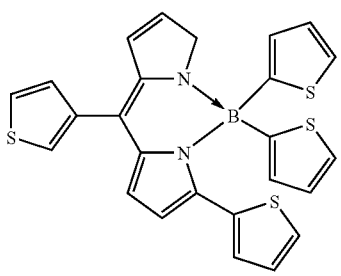

compound (4b)

reaction scheme (2)

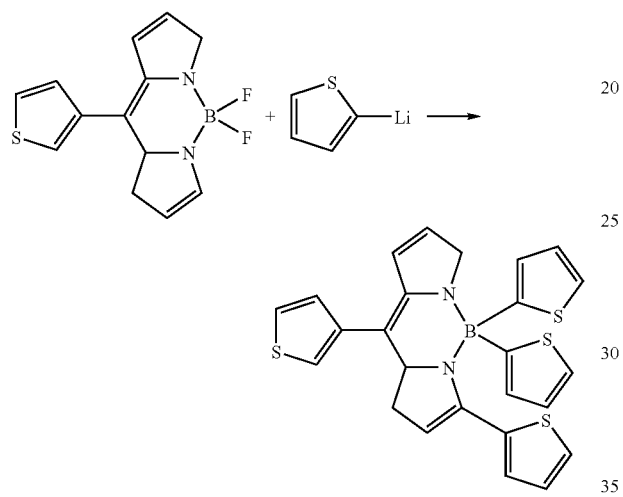

Compound (4b) was prepared by the same procedure as described in Example 1, except that compound (3b) which was prepared by a typical method known in the Journal of Chemical Crystallography 2007, 37, 315 (0.18 g, 0.65 mmol) was used as the starting material and amount of 2-thienyl lithium was 6.5 mL.

After termination of the reaction, it was observed that a portion of the mixture solution exhibited stronger red fluorescence with $R_f$ of about 0.8 from TLC. Compound (4b), that is, 3-(2-thienyl)-4,4-di(2-thienyl)-8-(3-thienyl)-4-bora-3a,4a-diaza-s-indacene in pure state was obtained by three times development of the mixture solution by passing it through a silica column and performing PTLC, respectively (0.12 g, yield: 35%). Melting point: 166° C. $^1$H NMR (CD$_2$Cl$_2$: δ 5.32) 7.79 (dd, $^4J_{H-H}$=3.0, $^4J_{H-H}$=1.2 Hz, 1H$_c$), 7.57 (d, J=3.0 Hz, 1H$_a$), 7.56 (m, 1H$_h$), 7.48 (dd, $^3J_{H-H}$=5.0, $^4J_{H-H}$=1.2 Hz, 1H$_b$), 7.30 (d, $^3J_{H-H}$=4.5 Hz, 1H$_d$), 7.29 (dd, $^3J_{H-H}$= 4.7, $^4J_{H-H}$=0.8 Hz, 2Hz), 7.24 (dd, $^3J_{H-H}$=5.0, $^4J_{H-H}$=1.1 Hz, 1H$_k$), 7.03 (d, $^3J_{H-H}$=obs, $^4J_{H-H}$=1.3 Hz, 1H$_f$), 7.02 (dd, $^3J_{H-H}$=3.4, $^4J_{H-H}$=1.0 Hz, 2H$_l$), 6.95. (m, 2H$_m$), 6.85 (d, $^3J_{H-H}$=4.5 Hz, 1H$_e$), 6.84 (dd, $^3J_{H-H}$=3.7, $^4J_{H-H}$=1.1 Hz, 1H$_i$), 6.73 (dd, $^3J_{H-H}$=5.1, $^4J_{H-H}$=3.7 Hz, 1H$_j$), 6.47 (dd, $^3$J=4.2, 1.9 Hz, 1H$_g$); $^{13}$C NMR (CD$_2$Cl$_2$: δ 53.8) 152.1 (m, 1C$_5$), 144.3 (dt, $^1J_{C-H}$=184.9, $^3J_{C-H}$=9.1 Hz, 1C$_h$), 139.7 (s, 1C$_2$), 136.9 (t, $^2J_{C-H}$=9.0 Hz, 1C$_3$), 135.4 (m, 1C$_1$), 134.6 (m, 1C$_6$), 133.0 (q, $^2J_{C-H}$=8.8 Hz, 1C$_4$), 131.9 (ddd, $^1J_{C-H}$=170.7, $^2J_{C-H}$=9.2, 1C$_i$), 130.9 (ddd, $^1J_{C-H}$=163.3, $^2J_{C-H}$=9.8, 1C$_1$), 130.5 (dm, $^1J_{C-H}$=171.9, 1C$_b$), 130.4 (dm, $^1J_{C-H}$=165.4 Hz, 1C$_d$), 129.6 (dm, $^1J_{C-H}$=171.0 Hz, 1C$_c$), 128.9 (dm, $^1J_{C-H}$=186.2 Hz, 1C$_k$), 127.9 (dm, $^1J_{C-H}$=161.0, 1C$_f$), 127.6 (dm, $^1J_{C-H}$=170.8, 1C$_j$), 127.5 (dm, $^1J_{C-H}$=168.7, 2C$_m$), 127.0 (ddd, $^1J_{C-H}$=184.2, $^2J_{C-H}$=10, $^3J_{C-H}$=7.8 Hz, 2C$_n$), 126.7 (dt, $^1J_{C-H}$=186.8, $^3J_{C-H}$=6.9 Hz, 1C$_a$), 122.1 (dd, $^1$; J$_{C-H}$=175.1, J$_{C-H}$=3.7 Hz, 1C$_e$), 118.3 (ddd, $^1J_{C-H}$=174.6, $^2J_{C-H}$=8.9, $^2J_{C-H}$=3.7 Hz, 1C$_g$). $^{11}$B NMR (BF$_3$ OEt$_2$: δ 0.00) −3.61 (s), MALDI-TOF m/z (M$^+$): 484.04 (calc.) 484.36 (obs.), Anal. Calc. for C$_{25}$H$_{17}$BN$_2$S$_4$: C 61.98, H 3.54, and N 5.78, found: C 62.63, H 4.21, and N 5.66.

EXAMPLE 3

Preparation of 3-(3-thienyl)-4,4-di(3-thienyl)-8-(2-thienyl)-4-bora-3a,4a-diaza-s-indacene [5a]

A compound (5a) was prepared by reacting a compound (3a) with 3-thienyl lithium according to the following reaction scheme 3:

compound (3a)

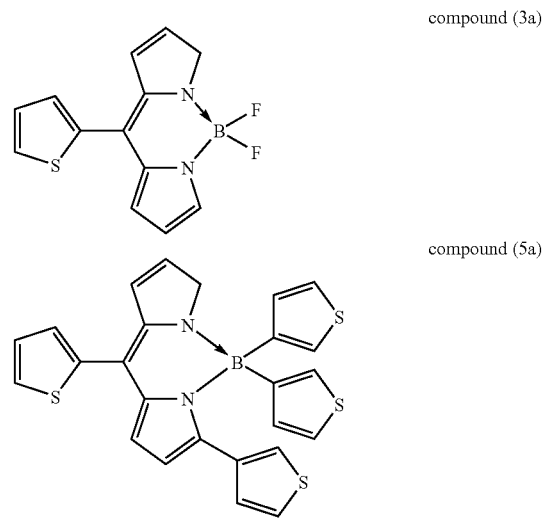

compound (5a)

reaction scheme (3)

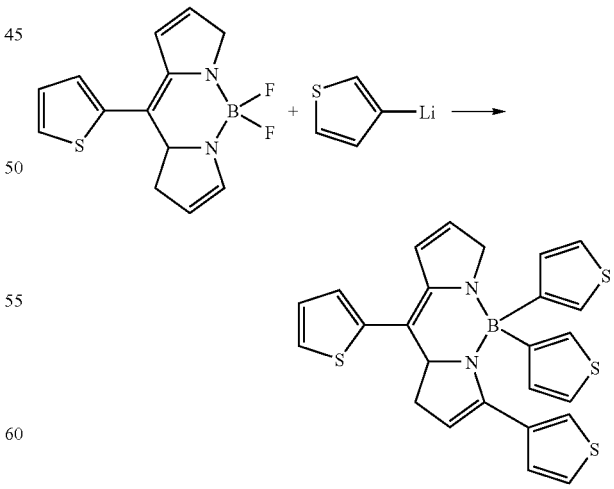

3-thienyl lithium was prepared by a typical method known in Karlsson, L. et. al., Chemica Scripta 1974, 6, 214-221. More particularly, 3-bromothiophene (1.6 mL, 0.017 mmol) was dissolved in 50 mL of ether anhydride and this mixture was agitated at −78° C. for 10 minutes under Ar atmosphere. By drop-wise adding 5.4 mL of a 2.5M diluted n-butyl lithium in hexane at 1 ml/sec to the agitated solution and again agitating the reaction mixture at −78° C. for 10 minutes under Ar atmosphere, 3-thienyl lithium was obtained.

Compound (3a) (0.46 g, 0.0017 mol) was dissolved in 12 mL of anhydrous THF and left without further treatment at room temperature. This solution containing compound (3a) was delivered through a cannula into a flask containing the above prepared 3-thienyl lithium solution and mixed together. The mixture solution was agitated at a constant temperature of −78° C. under Ar atmosphere. After 10 minutes and monitoring that compound (3a) was completely reacted by TLC, water was added to the mixture solution to terminate the reaction. Finally, the purification process described in Example 1 was applied to yield a pure compound of 3-(3-thienyl)-4,4-di(3-thienyl)-8-(2-thienyl)-4-bora-3a, 4a-diaza-s-indacene (5a) as a final product (0.088 g, yield: 11%). Melting point: 184° C.

$^1$H NMR (CD$_2$Cl$_2$: δ 5.32) 7.71 (dd, $^3J_{H-H}$=5.1, $^4J_{H-H}$=1.2 Hz, 1H$_b$), 7.61 (dd, $^3J_{H-H}$=3.7, $^4J_{H-H}$=1.2 Hz, 1H$_c$), 7.46 (d, $^3J_{H-H}$=4.4 Hz, 1H$_d$), 7.41 (m, 1H$_h$), 7.28 (m, 1H$_a$), 7.19 (dd, $^3J_{H-H}$=4.3, $^4J_{H-H}$=1.3 Hz, 1H$_f$), 7.15 (dd, $^3J_{H-H}$=4.8, $^3J_{H-H}$=2.7 Hz, 2H$_m$), 7.01 (m, 1H$_j$), 6.97 (m, 1H$_k$), 6.94 (dd, $^4J_{H-H}$=2.7, $^4J_{H-H}$=1.1 Hz, 2H$_n$), 6.89 (dd, $^3J_{H-H}$=4.8, $^4J_{H-H}$=1.1 Hz, 2H$_l$), 6.81 (dd, $^3J_{H-H}$=5.0, $^4J_{H-H}$=1.3 Hz, 2H$_i$), 6.74 (d, $^3J_{H-H}$=4.4 Hz, 1H$_e$), 6.46 (dd, $^3J_{H-H}$=4.2, $^4J_{H-H}$=1.8 Hz, 1H$_g$); $^{13}$C NMR (CD$_2$Cl$_2$: δ 53.8) 154.6 (t, $^1J_{C-H}$=8.2 Hz, 1C$_5$), 143.6 (dt, $^1J_{C-H}$=184.6, $^1J_{C-H}$=9.0 Hz, 1C$_h$), 138.0 (s, 1C$_2$), 136.4 (t, $^1J_{C-H}$=9.0 Hz, 1C$_3$), 135.6 (m, 1C$_1$), 133.4 (m, 1C$_6$), 133.1 (m, 1C$_4$), 132.8 (ddd, $^1J_{C-H}$=170.0, $^2J_{C-H}$=9.3, $^3J_{C-H}$=5.8 Hz, 1C$_c$), 132.2 (dm, $^1J_{C-H}$=152.1 Hz, 1C$_1$), 130.7 (dm, $^1J_{C-H}$=169.6 Hz, 1C$_d$), 130.5 (ddd, $^1J_{C-H}$=184.9, $^2J_{C-H}$=10.8, $^2J_{C-H}$=7.1 Hz, 1C$_b$), 129.2 (ddd, $^1J_{C-H}$=171.1, $^3J_{C-H}$=10, $^3J_{C-H}$=3.6 Hz, 1C$_i$), 128.1 (dm, $^1J_{C-H}$=180.9 Hz, 1C$_a$), 128.0 (dm, $^1J_{C-H}$=~170 Hz, 12C$_f$), 128.0 (dm, $^1J_{C-H}$=~170 Hz, 1C$_k$), 127.7 (ddd, $^1J_{C-H}$=160.8, $^3J_{C-H}$=8.5, $^3J_{C-H}$=4.2 Hz, 1C$_n$), 124.6 (ddd, $^1J_{C-H}$=183.2, J$_{C-H}$=4.7 Hz, 1C$_m$), 124.1 (ddd, $^1J_{C-H}$=187.6, J$_{C-H}$=6.2, J$_{C-H}$=4.7 Hz, 1C$_j$), 121.6 (dd, $^1J_{C-H}$=174.4, J$_{C-H}$=3.5 Hz, 1C$_e$), 117.8 (ddd, $^1J_{C-H}$=174.5, $^2J_{C-H}$=9.1, $^2J_{C-H}$=3.6 Hz, 1C$_g$). $^{11}$B NMR (BF$_3$ OEt$_2$: δ 0.00) −3.59 (s), MALDI-TOF m/z (M$^+$): 484.04 (calc.) 484.68 (obs.), Anal. Calc. for C$_{25}$H$_{17}$BN$_2$S$_4$: C 61.98, H 3.54, and N 5.78, found: C 63.68, H 3.82, and N 6.03.

EXAMPLE 4

Preparation of 3-(3-thienyl)-4,4-di(3-thienyl)-8-(3-thienyl)-4-bora-3a,4a-diaza-s-indacene [5b]

A compound (5b) was prepared by reacting a compound (3b) with 3-thienyl lithium according to the following reaction scheme 4:

compound (3b)

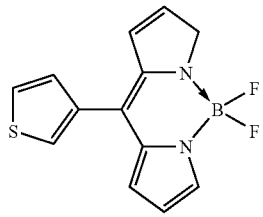

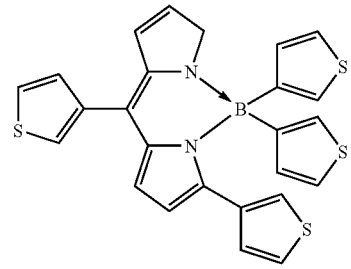

compound (5b)

reaction scheme (4)

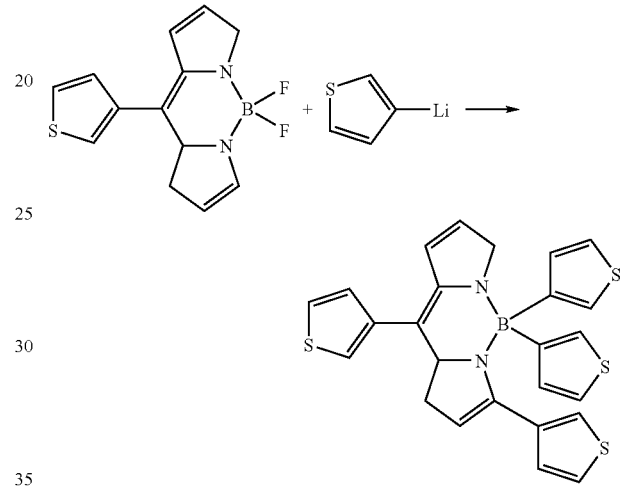

Compound (5b) was prepared by the same procedure as described in Example 3, except that compound (3b) (1.0 g, 3.65 mmol) was used instead of compound (3a).

Amount of the resulting compound (5b) was 0.15 g with yield of about 8.5%. Melting point: 178° C. $^1$H NMR (CD$_2$Cl$_2$: δ5.32) 7.78 (dd, $^4J_{H-H}$=3.0, $^4J_{H-H}$=1.2 Hz, 1H$_c$), 7.55 (m, 1H$_a$), 7.47 (dd, $^3J_{H-H}$=5.0, $^4J_{H-H}$=1.2 Hz, 1H$_b$), 7.43 (m, 1H$_h$), 7.30 (d, $^3J_{H-H}$=4.5 Hz, 1H$_d$), 7.17 (dd, $^3J_{H-H}$=4.7, $^4J_{H-H}$=2.7 Hz, 2H$_m$), 7.03 (d, $^3J_{H-H}$=obs, $^4J_{H-H}$=1.2 Hz, 1H$_f$), 7.02 (m, 1H$_j$), 6.98 (m, 1H$_k$), 6.96 (dd, J=2.7, 1.1 Hz, 2H$_n$), 6.91 (dd, J=4.8, 1.1 Hz, 2H$_l$), 6.83 (dd, $^3J_{H-H}$=5.0, $^4J_{H-H}$=1.4 Hz, 1H$_i$), 6.73 (d, $^3J_{H-H}$=4.5 Hz, 1H$_e$), 6.46 (dd, $^3J_{H-H}$=4.2, J$_{H-H}$=1.8 Hz, 1H$_g$); $^{13}$C NMR (CD$_2$Cl$_2$: δ 53.8) 154.3 (m, 1C$_5$), 152.4 (br, 1C$_7$), 143.4 (dt, $^1J_{C-H}$=184.4, $^3J_{C-H}$=9.0, 1C$_h$), 140.1 (s, 1C$_2$), 136.4 (t, $^1J_{C-H}$=9.0 Hz, 1C$_3$), 135.6 (m, 1C$_1$), 133.5 (m, 1C$_6$), 133.2 (d, $^1J_{C-H}$=8.7 Hz, 1C$_4$), 132.2 (ddd, $^1J_{C-H}$=164.9, $^2J_{C-H}$=10.5, $^3J_{C-H}$=4.9 Hz, C$_1$), 130.5 (ddd, $^1J_{C-H}$=173.0, $^2J_{C-H}$=8.5, $^3J_{C-H}$=4.7 Hz, 1C$_b$), 130.2 (dd, $^1J_{C-H}$=175.1, $^3J_{C-H}$=4.2 Hz, 1C$_d$), 129.4 (dm, $^1J_{C-H}$=185.8 Hz, 1C$_c$), 129.2 (ddd, $^1J_{C-H}$=170.5, $^2J_{C-H}$=8.5, $^3J_{C-H}$=4.1 Hz, 1C$_i$), 128.0 (ddd, $^1J_{C-H}$=128.0, $^3J_{C-H}$=8.5, $^3J_{C-H}$=4.4 Hz, 1C$_k$), 127.6 (dm, $^1J_{C-H}$=152.4 Hz, C$_n$), 127.5 (dm, $^1J_{C-H}$=195.4 Hz, 1C$_f$), 126.6 (dm, $^1J_{C-H}$=188.8 Hz, 1C$_a$), 124.6 (ddd, $^1J_{C-H}$=189.6, $^2J_{C-H}$=9.0, $^3J_{C-H}$=4.7 Hz, 2C$_m$), 124.1 (dt, $^1J_{C-H}$=187.6 Hz, $^3J_{C-H}$=6.3, 1C$_j$), 121.4 (dd, $^1J_{C-H}$=171.1, $^2J_{C-H}$=3.5 Hz, 1C$_e$), 117.7 (ddd, $^1J_{C-H}$=174.3, $^2J_{C-H}$=9.0, $^2J_{C-H}$=3.7 Hz, 1C$_g$). $^{11}$B NMR (BF$_3$ OEt$_2$: δ 0.00) −3.35 (s), MALDI-TOF m/z (M$^+$): 484.04 (calc.) 484.41 (obs.), Anal. Calc. for C$_{25}$H$_{17}$BN$_2$S$_4$: C 61.98, H 3.54, and N 5.78, found: C 62.56, H 3.82, and N 5.88.

EXAMPLE 5

Experiment for Selectivities of Substrates To Metal Ions

For UV ray-IR ray absorption spectroscopy and fluorescence spectroscopy, each of compounds (4a), (4b), (5a) and (5b) prepared in Examples 1 to 4, respectively was dissolved in $CH_3CN$ to prepare a solution with a molar concentration of $1 \times 10^{-5}$.

All metal ions used in the present invention were in the form of metal-perchlorates and dissolved in $CH_3CN$ and prepared with molar concentration of $1 \times 10^{-3}$. Such metal ions were $Zn^{2+}$, $Pb^{2+}$, $Mn^{2+}$, $Hg^{2+}$, $Cu^{2+}$, $Cs^+$, $Ca^{2+}$, $Cd^{2+}$ and $Ag^+$.

Compounds (4a), (4b), (5a) and (5b) were used to prepare mixture solutions of compound (4a)-metal ions, compound (4b)-metal ions, compound (5a)-metal ions and compound (5b)-metal ions, respectively, in order to make the mixture solutions have a constant stoichiometric ratio between metal ions of 1:1. Each mixture of solutions was monitored using both a UV-IR absorption spectrometer and a fluorescence spectrometer.

For compound (4b), a spectrum for $Cu^{2+}$ was remarkably varied and alteration of spectrum for $Hg^{2+}$ was also slightly observed, compared to other metal ions, although the alteration was only slight. Alternatively, compounds (4a), (5a) and (5b) exhibited alteration of UV-IR absorption spectroscopic spectra for $Cu^{2+}$ and $Hg^{2+}$ even though the alteration was much less, compared to compound (4b) (see FIGS. 2a, 2b, 2c and 2d).

Similar results were demonstrated for fluorescence spectra as shown in FIGS. 3a to 3d.

From results of this experiment, it was understood that the boron-dipyrrin compound with four substituted thienyl groups, three in the form of a scorpion, according to the present invention have selectivities to $Cu^{2+}$ and $Hg^{2+}$. In particular, compound (4b) showed color variation from pink to colorless dependent on $Cu^{2+}$ content and increase of fluorescent levels by UV radiation. On the other hand, $Hg^{2+}$ added to compound (4b) had less influence on variation of colors and alteration of fluorescent levels as shown in FIGS. 4a and 4b.

EXAMPLE 6

Experiment for $Cu^{2+}$ and $Hg^{2+}$ Detection Limits

In order to determine detection limits for $Cu^{2+}$, each compound (4a-5b) was dissolved in $CH_3CN$ to form a solution with molar concentration of $1 \times 10^{-5}$. 3 mL of the solution was plated in a quartz cell and UV-IR absorption spectrum of the solution was monitored at regular time intervals while titrating a $Cu^{2+}$ solution by a micropipette.

As shown in FIGS. 5a to 5d, the above prepared solution containing each of compounds (4a-5b) exhibited alteration in spectra even with only 10 μL of the $Cu^{2+}$ solution with molar concentration of $1 \times 10^{-3}$, which equates to 270 ppb.

The same procedure was applied to $Hg^{2+}$ detection limits in compounds (4a), (4b), (5a) and (5b).

More particularly, in order to determine detection limit for $Hg^{2+}$, each of compounds (4a), (4b), (5a) and (5b) was dissolved in $CH_3CN$ to prepare a solution with molar concentration of $1 \times 10^{-5}$ and UV-IR absorption spectrum of the solution was monitored at regular time intervals while adding $Hg^{2+}$ to the solution. From a result of the monitoring, it was demonstrated that variations in wavelengths and spectra were continued dependent on amount of $Hg^{2+}$ added to the solution.

The $Hg^{2+}$ detection limit in each of compounds (4a), (4b), (5a) and (5b) was 20 μL for a $Hg^{2+}$ solution with molar concentration of $1 \times 10^{-3}$, which equates to 1.7 ppm.

EXAMPLE 7

Experiment for $Cu^{2+}$ Bonding Reversibility

This experiment is to identify that the present inventive compounds are potentially useable chemosensors by determining the bonding reversibility of each of compounds (4a), (4b), (5a) and (5b), characterized in that compound is combined with $Cu^{2+}$ or $Hg^{2+}$, then, returned to original coordinate structure thereof.

Using compounds (4b) and (5b) selected as representative ones, the experiment for bonding reversibility was performed by UV-IR spectroscopy.

Compound (4b) was dissolved in $CH_3CN$ to prepare a solution with molar concentration of $5 \times 10^{-5}$ (abbrev. to "compound solution") and a $Cu^{2+}$ solution was prepared with molar concentration of $5 \times 10^{-3}$ by dissolving $Cu^{2+}$ in $CH_3CN$. $Na_4EDTA$ (ethylenediamine tetraacetate sodium salt) was dissolved in distilled water to have a 0.01 molar concentration. 1 mL of compound (4b) containing solution was added into each of five (5) sample bottles. The bottle #1 contained only compound solution, the bottle #2 contained $Cu^{2+}$ as well as compound solution, in relative molar ratio of 15 times compound solution. The bottle #3 further contained $Na_4EDTA$ in relative molar ratio of 30 times compound solution in addition to the same content as in the bottle #2. For the bottle #4, $Na_4EDTA$ in relative molar ratio of 30 times compound solution was first added to compound solution in the bottle, sufficiently shaken, and. $Cu^{2+}$ in relative molar ratio of 15 times that of the compound solution was further added to the mixture. Lastly, the bottle #5 contained a mixture of the compound solution and $Na_4EDTA$ in relative molar ratio of 30 times the compound solution.

In order to regulate concentrations of compounds (4b) in all of the sample bottles to a constant level, $CH_3CN$ buffer was added to make each of samples in the bottles to have a volume of 2.5 mL. Results of the bonding reversibility experiments were obtained by comparing UV-IR absorption spectroscopic spectra between the five samples.

Figure 6:
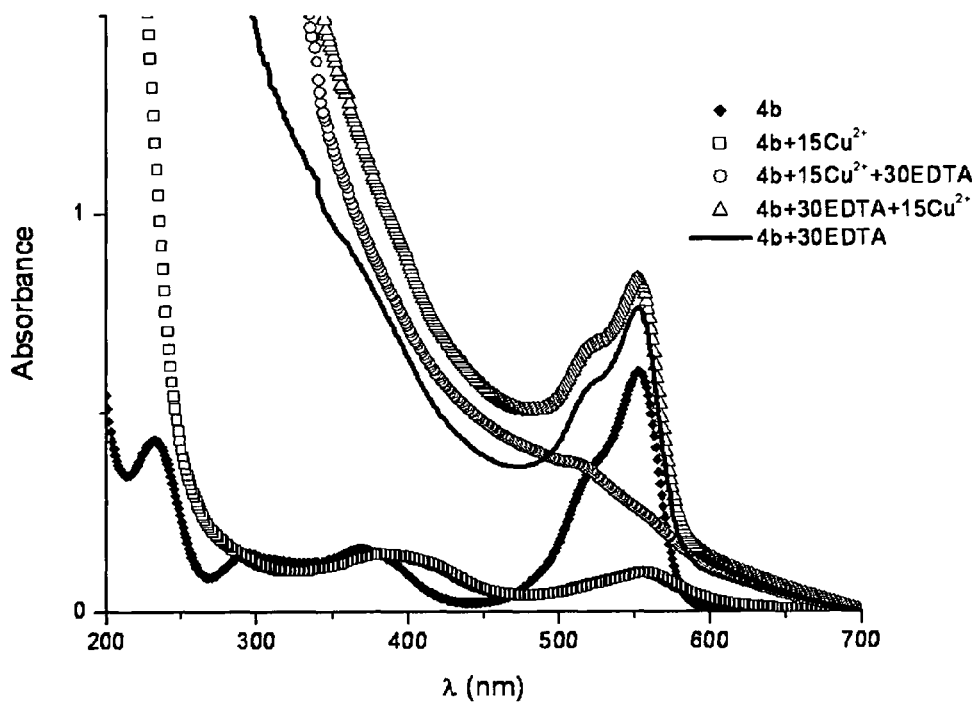
FIG. 6 shows absorption spectra illustrating binding reversibilities between compound (4b) and a copper ion compound by EDTA (ethylenediamine tetraacetate) addition.

As shown in FIG. 6, it was found that the pattern of original absorption spectroscopic spectrum of compound (4b) is considerably varied if compound (4b) is combined with $Cu^{2+}$. However, the sample #3 (in the bottle #3) containing EDTA showed additional change in the pattern of the absorption spectroscopic spectrum compared to the sample #2 (in the bottle #2), although the additionally changed pattern was not exactly identical to the original pattern.

Figure 7:
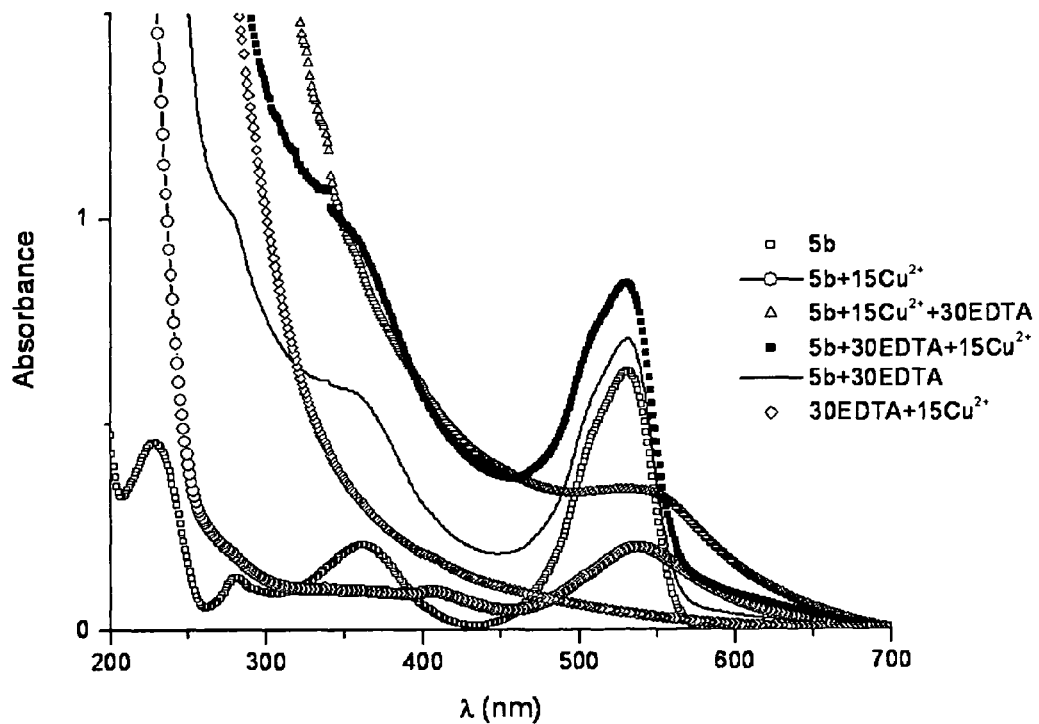
FIG. 7 shows absorption spectra illustrating bonding reversibilities between compound (5b) and a copper ion compound by EDTA addition.

The same experiment was applied to compound (5b) under the same conditions as shown in FIG. 7. Both of the samples, that is, the solutions containing compounds (4b) and (5b), respectively, became muddy by addition of EDTA. Therefore, even if EDTA added to each of the solutions affects the variation of absorption spectroscopic spectrum, such variation is expected to be uncertain, compared to the original spectrum of compound (4b) and (5b), due to turbidity of the sample.

EXAMPLE 8

Experiment for $Hg^{2+}$ Bonding Reversibility

This experiment was performed by using KI to determine the bonding reversibility of each of samples containing compounds (4b) and (5b) combined with $Hg^{2+}$, respectively.

It is well known that mercuric ions can be easily combined with iodide anions.

Similar to the procedures described in Example 7, 1 mL of compound (4b) containing solution was added in each of five sample bottles. The bottle #1 contained only the compound solution, the bottle #2 contained $Hg^{2+}$ as well as the compound solution, in relative molar ratio of 15 times the compound solution. The bottle #3 further contained KI relative molar ratio of 30 times the compound solution in addition to the same content as in the bottle #2. For the bottle #4, KI in relative molar ratio of 30 times the compound solution was first added to the compound solution in the bottle, sufficiently shaken, and $Hg^{2+}$ in relative molar ratio of 15 times the compound solution was further added to the mixture. Lastly, the bottle #5 contained a mixture of the compound solution and KI in relative molar ratio of 30 times the compound solution.

In order to regulate molar concentrations of compound (4b) in all of the sample bottles to a constant level, $CH_3CN$ buffer was added to make each of samples in the bottles to have a volume of 3 mL.

For compound (5b), the same samples were prepared. Herein, each of the compounds (4b) and (5b) was dissolved in $CH_3CN$ to prepare a solution with molar concentration of $5\times10^{-5}$. An $Hg^{2+}$ solution was prepared with molar concentration of $1\times10^{-3}$ by dissolving $Hg^{2+}$ in $CH_3CN$. KI was dissolved in distilled water to have molar concentration of $1\times10^{-3}$.

Figure 8:
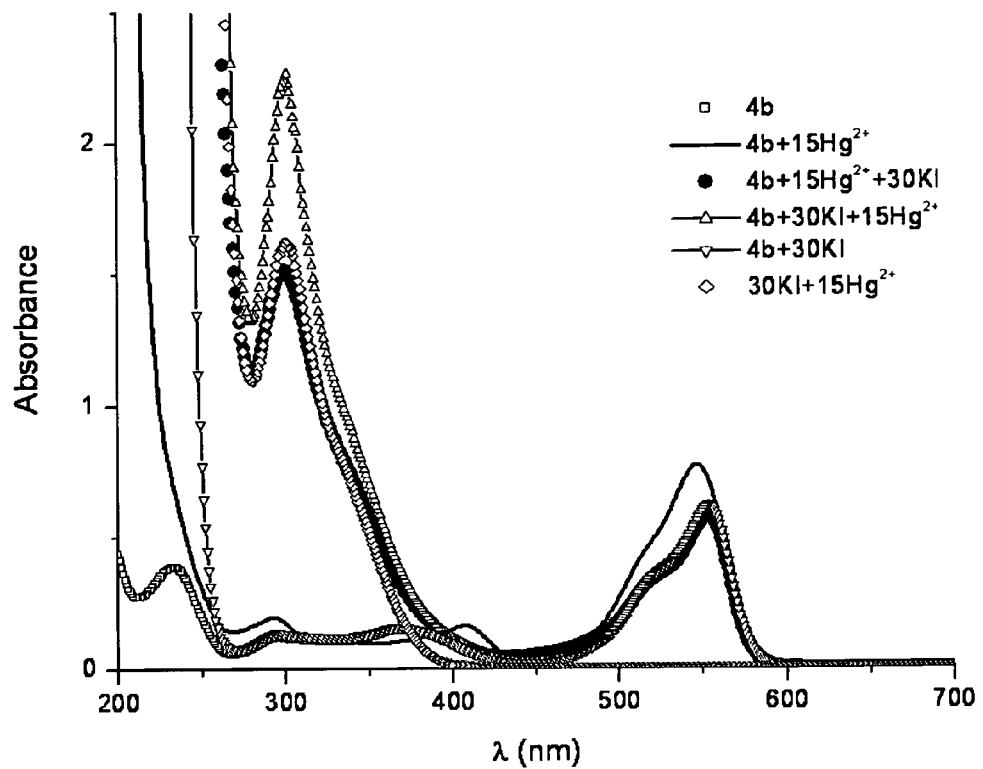
FIG. 8 shows absorption spectra illustrating bonding reversibilities between compound (4b) and a copper ion compound by KI (potassium iodide) addition.
Figure 9:
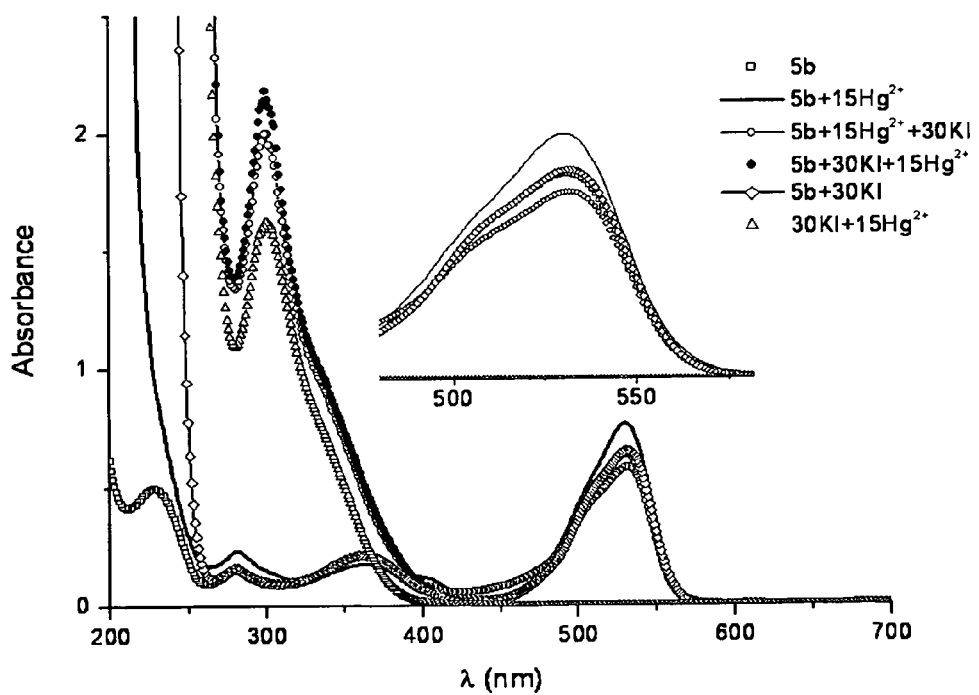
FIG. 9 shows absorption spectra illustrating bonding reversibilities between compound (5b) and a copper ion compound by KI addition.

All of the prepared samples containing $Hg^{2+}$ were clear. As shown in FIGS. 8 and 9, each of the compounds (4b) and (5b) combined with $Hg^{2+}$ released $Hg^{2+}$ by adding KI, thereby exhibiting the pattern of absorption spectroscopic spectrum and wavelength substantially identical to original ones of compound (4b) or (5b). As a result, it is obvious that compounds (4b) or (5b) have bonding reversibility for $Hg^{2+}$. This result is very important and suggests that the boron-dipyrrin compound having thienyl group proposed by the present invention has reversible properties under mild conditions required for chemosensors.

The present inventive boron-dipyrrin compound having thienyl group is useful for detecting metal ions, especially, copper ions $Cu^{2+}$ and/or mercuric ions $Hg^{2+}$, and can be efficiently applied in manufacturing chemosensors for removal of environmental pollutants such as $Cu^{2+}$ and/or $Hg^{2+}$.

While the present invention has been described with reference to the preferred embodiments and examples, it will be understood by those skilled in the art that various modifications and variations may be made therein without departing from the scope of the present invention as defined by the appended claims.

What is claimed is:

1. A boron-dipyrrin compound having thienyl group represented by the following formula (1):

$$3\text{-(R)-4,4-di(R)-8-(R)-4-bora-}3a,4a\text{-diaza-}s\text{-indacene} \quad \text{formula (1)}$$

wherein R is 2-thienyl group or 3-thienyl group.

2. The compound according to claim 1, wherein formula (1) is obtained by substituting difluoro group and eighth (8) carbon site of a compound represented by the following formula (2), with 2-thienyl group or 3-thienyl group:

$$3\text{-(R)-4,4-difluoro-4-bora-}3a,4a\text{-diaza-}s\text{-indacene} \quad \text{formula (2)}$$

wherein R is any one selected from the group consisting of 2-thienyl group, 3-thienyl group, furyl ($OC_4H_3$) group and selyl ($SeC_4H_3$) group.

* * * * *